United States Patent
Kepler et al.

(10) Patent No.: US 10,485,902 B2
(45) Date of Patent: Nov. 26, 2019

(54) ANTIBIOTIC DRUG RELEASE SHEATH

(71) Applicants: Thomas Jefferson University, Philadelphia, PA (US); Drexel University, Philadelphia, PA (US)

(72) Inventors: Christopher K. Kepler, Philadelphia, PA (US); Alex Michael Sevit, Philadelphia, PA (US); Steven Michael Kurtz, Philadelphia, PA (US); Noreen J. Hickok, Philadelphia, PA (US); Flemming Forsberg, Philadelphia, PA (US); John R. Eisenbrey, Philadelphia, PA (US)

(73) Assignees: Thomas Jefferson University, Philadelphia, PA (US); Drexel University, Philadelphia, PA (US)

(*) Notice: Subject to any disclaimer, the term of this patent is extended or adjusted under 35 U.S.C. 154(b) by 74 days.

(21) Appl. No.: 15/250,020

(22) Filed: Aug. 29, 2016

(65) Prior Publication Data

US 2017/0056565 A1    Mar. 2, 2017

Related U.S. Application Data

(60) Provisional application No. 62/211,388, filed on Aug. 28, 2015.

(51) Int. Cl.
*A61M 37/00* (2006.01)
*A61M 31/00* (2006.01)
(Continued)

(52) U.S. Cl.
CPC .......... *A61L 31/14* (2013.01); *A61B 17/7061* (2013.01); *A61B 17/7067* (2013.01);
(Continued)

(58) Field of Classification Search
CPC ......... A61L 2300/406; A61L 2300/602; A61B 17/7067; A61B 17/7061; A61M 37/0092; A61K 41/0028; A61K 9/0009
See application file for complete search history.

(56) References Cited

U.S. PATENT DOCUMENTS

| 7,358,226 B2 | 4/2008 | Dayton et al. |
| 2001/0038912 A1 | 11/2001 | Billarant et al. |

(Continued)

FOREIGN PATENT DOCUMENTS

WO    2003034975 A2    5/2003

OTHER PUBLICATIONS

Pitt, W.G., et al., "Ultrasound increases the rate of bacterial cell growth", Biotechnology Progress, vol. 19, No. 3, pp. 1038-1044, 2003.

(Continued)

*Primary Examiner* — Rebecca E Eisenberg
(74) *Attorney, Agent, or Firm* — Saul Ewing Arnstein & Lehr LLP; Kathryn Doyle; Brian R. Landry

(57) ABSTRACT

An implantable medical device having a sheath formed of a polymer material, wherein the sheath forms a reservoir attached to or around the implantable medical device, and wherein the reservoir is sealed with a biocompatible pressure responsive coating; wherein the biocompatible coating is stable for at least 7-day post implantation into a body, and can be mechanically ruptured by application of an exterior pressure generating force.

18 Claims, 6 Drawing Sheets

Lateral View
Spinal Hardware

(51) Int. Cl.

| | |
|---|---|
| *A61L 31/14* | (2006.01) |
| *A61L 31/06* | (2006.01) |
| *A61L 31/16* | (2006.01) |
| *A61B 17/70* | (2006.01) |
| *A61L 31/10* | (2006.01) |

(52) U.S. Cl.
CPC ............... *A61L 31/06* (2013.01); *A61L 31/10* (2013.01); *A61L 31/16* (2013.01); *A61L 2300/602* (2013.01)

(56) References Cited

U.S. PATENT DOCUMENTS

| | | | | |
|---|---|---|---|---|
| 2002/0160175 | A1* | 10/2002 | Pirhonen | A61F 2/2803 428/297.4 |
| 2007/0016163 | A1* | 1/2007 | Santini, Jr. | A61C 8/0012 604/500 |
| 2007/0141106 | A1* | 6/2007 | Bonutti | A61B 17/0401 424/423 |
| 2011/0178465 | A1* | 7/2011 | Boyd | A61B 17/60 604/175 |
| 2015/0202349 | A1 | 7/2015 | Emanuel | |

OTHER PUBLICATIONS

Poelstra, K.A., et al., "A novel spinal implant infection model in rabbits", Spine, vol. 25, No. 4, pp. 406-410, 2000.
Prasad, Y.V.R., et al., "Enhanced intestinal absorption of vancomycin with Labrasol and d-α-tocopheryl PEG 1000 succinate in rats", International Journal of Pharmaceutics, vol. 250, No. 1, pp. 181-190, 2003.
Rae, P.J., et al., "The mechanical properties of poly(ether-ether-ketone) (PEEK) with emphasis on the large compressive strain response", Polymer, vol. 48, No. 2, pp. 598-615, 2007.
Sevit, A., et al., "Development of an ultrasound-sensitive antimicrobial platform for reducing infection after spinal stabilization surgery", Ultrasonics Symposium (IUS), IEEE International, pp. 1045-1048, 2014.
Sevit, A.M., et al., "Antibiotic Drug Release PEEK Clip to Combat Surgical Site Infection in Spinal Fusion Surgery", 2nd International PEEK Conference, Spine, pp. 53-54, 2015.
Smith, A.W., "Biofilms and antibiotic therapy: is there a role for combating bacterial resistance by the use of novel drug delivery systems?", Adv Drug Deliv Rev, vol. 57, No. 10, pp. 1539-1550, 2005.
Standard Practice for Characterization of Particles, ASTM F1877-05, ASTM International, 2005.
Stewart, S., et al., "Vancomycin-Modified Implant Surface Inhibits Biofilm Formation and Supports Bone-Healing in an Infected Osteotomy Model in Sheep: A Proof-of-Concept Study", The Journal of Bone and Joint Surgery, vol. 94, No. 15, pp. 1406-1415, 2012.
Trampuz, A., et al., "Molecular and antibiofilm approaches to prosthetic joint infection", Clinical Orthopaedics & Related Research, vol. 414, pp. 69-88, 2003.
Trampuz, A., et al., "Sonication of removed hip and knee prostheses for diagnosis of infection", The New England Journal of Medicine, vol. 357, No. 7, pp. 654-663, 2007.
Usacheva, M.N., et al., "Comparison of the methylene blue and toluidine blue photobactericidal efficacy against gram-positive and gram-negative microorganisms", Lasers Surg Med, vol. 29, No. 2, pp. 165-173, 2001.
Vancomycin Solubility Study, Division of Product Quality Research, Office of Testing and Research Center for Drug Evaluation and Research Food and Drug Administration, 17 pages, Feb. 5, 2008.
Walker, J.N., et al., "The *Staphylococcus aureus* ArIRS two-component system is a novel regulator of agglutination and pathogenesis", PLOS Pathogens, vol. 9, No. 12, e1003819, 2013.
Weinstein, M.A., et al., "Postoperative spinal wound infection: a review of 2,391 consecutive index procedures", J Spinal Disord, vol. 13, No. 5, pp. 422-426, 2000.
Yu, X., et al., "The effect of temperature and pH on the solubility of quinolone compounds: estimation of heat of fusion", Pharm. Res., vol. 11, No. 4, pp. 522-527, 1994.
Zimmerli, W., et al., "Pathogenesis of implant-associated infection the role of the host", Seminars in Immunopathology, vol. 33, No. 3, pp. 295-306, 2011.
Antoci, V., Jr., et al., "Vancomycin covalently bonded to titanium alloy prevents bacterial colonization", Journal of Orthopaedic Research, vol. 25, pp. 858-866, 2007.
Antoci, V., Jr., et al., "Covalently attached vancomycin provides a nanoscale antibacterial surface", Clin Orthop Relat Res, vol. 461, pp. 81-87, 2007.
Antoci, V., Jr., et al., "Vancomycin bound to Ti rods reduces periprosthetic infection: preliminary study", Clin Orthop Relat Res, vol. 461, pp. 88-95, 2007.
Antoci, V., Jr., et al., "Antibiotics for local delivery systems cause skeletal cell toxicity in vitro", Clin Orthop Relat Res, vol. 462, pp. 200-206, 2007.
Beiner, J.M., et al., "Postoperative wound infections of the spine", Neurosurg. Focus, vol. 15, No. 3, e14, 2003.
Bernabeu, E., et al., "Vitamin E TPGS Used as Emulsifier in the Preparation of Nanoparticulate Systems", Journal of Biomaterials and Tissue Engineering, vol. 3, pp. 122-134, 2013.
Bible, J.E., et al., "Postoperative infections of the spine", The American Journal of Orthopedics, vol. 40, No. 12, pp. E264-271, 2011.
Bjerkan, G., et al., "Sonication is superior to scraping for retrieval of bacteria in biofilm on titanium and steel surfaces in vitro", Acta Orthopaedica, vol. 80, pp. 245-250, 2009.
Calderone, R.R., et al., "Overview and classification of spinal infections", Orthop Clinics North American, vol. 27, pp. 1-8, 1996.
Calderone, R.R., et al., "Outcome assessment in spinal infections", Orthop Clinics North America, vol. 27, pp. 201-205, 1996.
Carmen, J.C., et al., "Ultrasonically enhanced vancomycin activity against *Staphylococcus epidermidis* biofilms in vivo", J. Biomater Appl, vol. 18, No. 4, pp. 237-245, 2004.
Carmen, J.C., et al., "Ultrasonic-enhanced gentamicin transport through colony biofilms of Pseudomonas aeruginosa and *Escherichia coli*", J Infect Chemother, vol. 10, No. 4, pp. 193-199, 2004.
Chaudhary, S.B., et al., "Postoperative Spinal Wound Infections and Postprocedural Diskitis", The Journal of Spinal Cord Medicine, vol. 30, No. 5, pp. 441-451, 2007.
Chivers, R.A., et al., "The effect of molecular weight and crystallinity on the mechanical properties of injection molded poly(aryl-ether-ether-ketone) resin", Polymer, vol. 35, No. 1, pp. 110-116, 1994.
Collins, I., et al., "The diagnosis and management of infection following instrumented spinal fusion", Eur Spine J, vol. 17, pp. 445-450, 2008.
Collis, J., et al., "Cavitation microstreaming and stress fields created by microbubbles", Ultrasonics, vol. 50, No. 2, pp. 273-279, 2010.
Conner-Kerr, T., et al., "The effects of low-frequency ultrasound (35 kHz) on methicillin-resistant *Staphylococcus aureus* (MRSA) in vitro", Ostomy Would Management, vol. 56, No. 5, pp. 32-42, 2010.
Corveleyn, S., et al., "Formulation of a lyophilized dry emulsion tablet for the delivery of poorly soluble drugs", International Journal of Pharmaceutics, vol. 166, No. 1, pp. 65-74, 1998.
Costerton, J.W., et al., "Biofilm in implant infections: its production and regulation", International Journal of Artificial Organs, vol. 28, No. 11, pp. 1062-1068, 2005.
Cutting, K.F., "Wound exudate: composition and functions", Br. J. Community Nurs., vol. 8 (9Suppl), pp. 4-9, 2003.
Dastgheyb, S., et al., "Effect of Biofilms on Recalcitrance of Staphylococcal Joint Infection to Antibiotic Treatment", J Infect Dis, vol. 211, No. 4, pp. 641-650, 2015.
Eisenbrey, J.R., et al., "Development and optimization of a doxorubicin loaded poly(lactic acid) contrast agent for ultrasound directed drug delivery", J Control Release, vol. 143, No. 1, pp. 38-44, 2010.

(56) References Cited

OTHER PUBLICATIONS

Emohare, O., et al., "Cost savings analysis of intrawound vancomycin powder in posterior spinal surgery", The Spine Journal, vol. 14, No. 11, pp. 2710-2715, 2014.

Ensing, G.T., et al., "The combination of ultrasound with antibiotics released from bone cement decreases the viability of planktonic and biofilm bacteria: an in vitro study with clinical strains", Journal of Antimicrobial Chemotherapy, vol. 58, pp. 1287-1290, 2006.

Ferry, T., et al., "The challenge of infection prevention in spine surgery: an update", European Journal of Orthopaedic Surgery & Traumatology, vol. 23, Supplement 1, pp. 15-19, 2013.

Freeman, T.A., et al., "Micro-CT analysis with multiple thresholds allows detection of bone formation and resorption during ultrasound-treated fracture healing", Journal of Orthopaedic Research, vol. 27, pp. 673-679, 2009.

Ghobrial, G.M., et al., "Intraoperative vancomycin use in spinal surgery: single institution experience and microbial trends", Spine, vol. 39, No. 7, pp. 550-555, 2014.

Go, J.L., et al., "Spine infections", Neuroimaging Clinics of North America, vol. 22, No. 4, pp. 755-772, 2012.

Godi, S.S., et al., "Comparative effectiveness and cost-benefit analysis of local application of vancomycin powder in posterior spinal fusion for spine trauma", J. Neurosurg Spine, vol. 19, pp. 331-335, 2013.

Gunja, N.J., et al., "Biodegradable materials in arthroscopy", Sports Medicine & Arthroscopy Review, vol. 14, No. 3, pp. 112-119, 2006.

He, N., et al., "Enhancement of vancomycin activity against biofilms by using ultrasound-targeted microbubble destruction", Antimicrobial Agents and Chemotherapy, vol. 55, No. 11, pp. 5331-5337, 2011.

Hegde, V., et al., "Management of postoperative spinal infections", World J Orthop, vol. 3, No. 11, pp. 182-189, 2012.

Hickok, N.J., et al., "Immobilized antibiotics to prevent orthopaedic implant infections", Adv Drug Deliv Rev, vol. 64, No. 12, pp. 1165-1176, 2012.

Hill, B.W., et al., "The use of vancomycin powder reduces surgical reoperation in posterior instrumented and noninstrumented spinal surgery", Acta Neurochirurgica, vol. 156, No. 4, pp. 749-754, 2014.

Johnson, P.J.T, et al., "Pharmacodynamics, population dynamics, and the evolution of persistence in *Staphylococcus aureus*", PLOS Genet, vol. 9, No. 1, pp. 1-13, e1003123, 2013.

Katzer, A., et al., "Polyetheretherketone-cytotoxicity and mutagenicity in vitro", Biomaterials, vol. 23, No. 8, pp. 1749-1759, 2002.

Ketonis, C., et al., "Topographic features retained after antibiotic modification of Ti alloy surfaces", Clinical Orthopaedics and Related Research, vol. 467, No. 7, pp. 1678-1687, 2009.

Ketonis, C., et al., "Bacterial colonization of bone allografts: establishment and effects of antibiotics", Clinical Orthopaedics and Related Research, vol. 468, No. 8, pp. 2113-2121, 2010.

Ketonis, C., et al., "Vancomycin bonded to bone grafts prevents bacterial colonization", Antimicrobial Agents and Chemotherapy, vol. 55, No. 2, pp. 487-494, 2011.

Keren, I., et al., "Persister eradication: lessons from the world of natural products", Methods in Enzymology, vol. 517, pp. 387-406, 2012.

Kim, B., et al., "Antibiotic Microbial Prophylaxis for Spinal Surgery: Comparison between 48 and 72-Hour AMP Protocols", Asian Spine J, vol. 4, No. 2, pp. 71-76, 2010.

Kurtz, S.M., et al., "PEEK Biomaterials in trauma, orthopedic, and spinal implants", Biomaterials, vol. 28, No. 32, pp. 4845-4869, 2007.

Kurtz, S.M., et al., "Infection risk for primary and revision instrumented lumbar spine fusion in the Medicare population", J Neurosurg Spine, vol. 17, pp. 342-347, 2012.

Kurtz, S.M., et al., "Retrieval analysis of PEEK rods for posterior fusion and motion preservation", European Spine Journal, vol. 22, No. 12, pp. 2752-2759, 2013.

Lewis, K., "Multidrug tolerance of biofilms and persister cells", Current Topics in Microbiology & Immunology, vol. 322, pp. 107-131, 2008.

Liu, X., et al., "Acoustic microstreaming around an isolated encapsulated microbubble", J. Acoust. Soc. Am., vol. 125, pp. 1319-1330, 2009.

Malone, C.L., et al., "Fluorescent reporters for *Staphylococcus aureus*", Journal of Microbiological Methods, vol. 77, No. 3, pp. 251-260, 2009.

Molinari, R.W., et al., "Prophylactic intraoperative powdered vancomycin and postoperative deep spinal wound infection: 1,512 consecutive surgical cases over a 6-year period", European Spine Journal, vol. 21, Supplement 4, pp. 476-482, 2012.

O'Neill, K.R., et al., "Reduced surgical site infections in patients undergoing posterior spinal stabilization of traumatic injuries using vancomycin powder", Spine J, vol. 11, No. 7, pp. 641-646, 2011.

Otto, M., "*Staphylococcus* epidermidis-the 'accidental' pathogen", Nature Reviews Microbiology, vol. 7, pp. 555-567, 2009.

\* cited by examiner

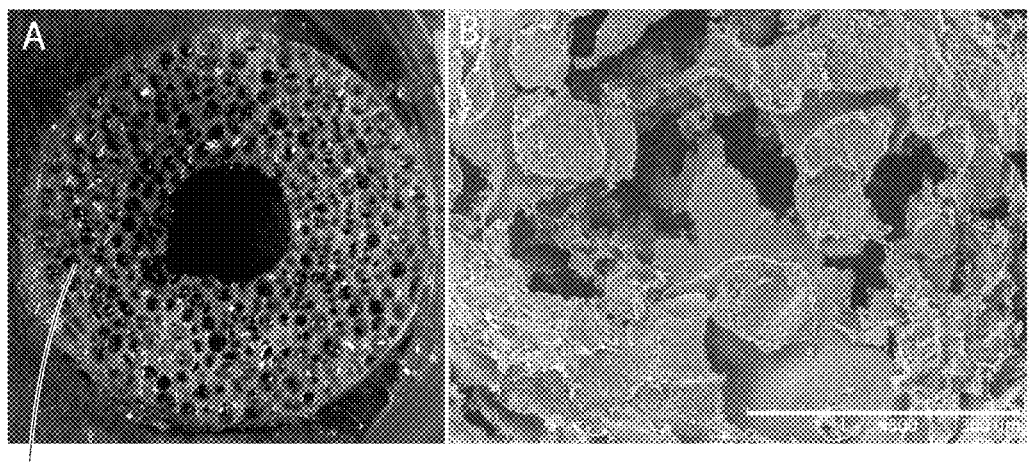
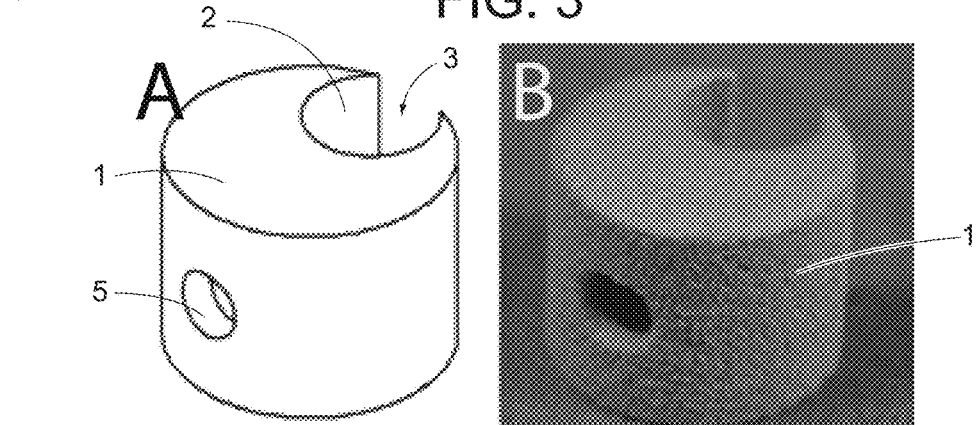
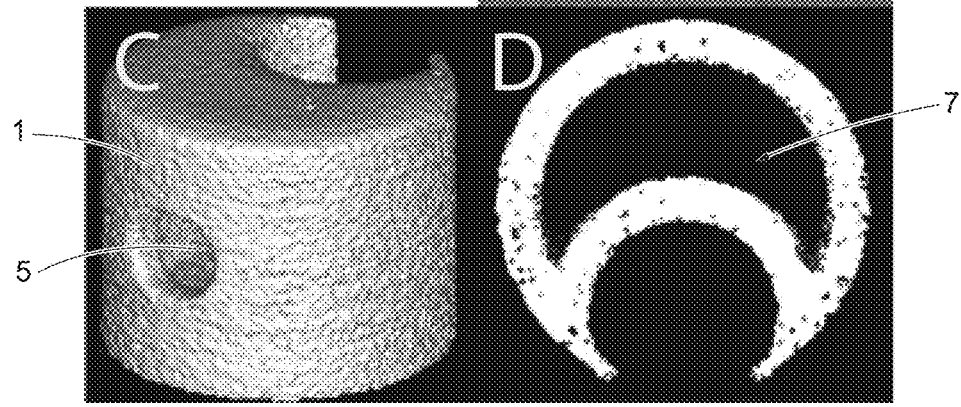
FIG. 3
FIG. 4

ANTIBIOTIC DRUG RELEASE SHEATH

CROSS-REFERENCE TO RELATED APPLICATION

The present application claims benefit under 35 U.S.C. 119(e) of U.S. Provisional Application No. 62/211,388, filed Aug. 28, 2015, the contents of which are incorporated herein by reference in its entirety.

FIELD OF INVENTION

The present application is generally related to devices and methods thereof to prevent infections during the peri-operative period.

BACKGROUND OF INVENTION

Infection is a catastrophic and too frequent complication of many surgical procedures. In the case of surgical procedures that introduce a foreign substance into the body, there is increased risk of such infection that leads to failure of the surgical procedure or dangerous infections in the body. For example, in spinal surgery several existing measures to prevent infection are only partially successful, despite the best interests and intentions of medical professionals. Spinal surgical sites are prone to bacterial colonization due to hardware presence, long surgical times, and the creation of a "dead" space ($\geq 5$ cm$^3$) that is filled with wound exudate. Following trauma, there is both immune suppression and polymicrobial contamination with an accompanying increase in infection risk.

Importantly, bacteria that are adherent to spinal hardware or in floating biofilms in wound fluid become recalcitrant to antibiotic therapy[7,8]. Despite aggressive peri-operative antibiotic treatments, between 1 in 20 and 1 in 100 patients undergoing spinal surgery develop an infection. Hardware removal and implantation of an antibiotic spacer is not possible in spinal infection, requiring treatment in the presence of hardware. Because spinal infections must be treated in the presence of the hardware, the current standard of care includes irrigation, aggressive debridement of the infected soft tissues, and prolonged antibiotic treatment, often resulting in extended pain, delayed wound and bone healing, disability, and, in the worst cases, death.

One method to minimize infection is for spinal surgeons to place ~1 g of vancomycin (VAN) during closure[1-4] thereby lowering morbidity and mortality and saving ~$35 k-114 k/affected patient[5,6]. Importantly, these infections are assumed to be caused by adherent bacteria which are markedly recalcitrant to antibiotic treatment[9,10], thus the use of supratherapeutic levels of VAN peri-operatively. However, the efficacy of this practice is currently unclear. Even with high VAN levels, decreases in spinal infection rates are only modest. Perhaps because VAN is active against only Gram-positive pathogens[3] such as *S. aureus*, VAN packed around the implant prior to closure may[1,2,4] or may not[3] decrease contaminating bacteria. Thus, despite this aggressive prophylaxis with VAN[3], ~1-4% of spinal surgeries may still become infected.

Spinal infection rates are >4%. After the surgical site has been closed and prophylactic antibiotics are depleted; surgeons do not currently have a means to locally continue prophylaxis to combat establishment of these infections. Other treatment choices are limited as debridement of the spine to remove adherent bacteria cannot be undertaken, local antibiotic injection could introduce additional bacteria, and antibiotic-eluting spacers have not been developed for spinal applications.

Therefore a focus on new ways to create implant systems that prevent bacterial colonization is essential. Furthermore to be most effective, new treatments must eradicate pathogens before their adherence to the implant surface attenuates antibiotic effectiveness and immune susceptibility. The work in this application addresses this need for a simple device to continue prophylaxis and to lower the infection rates associated with spinal fusions.

SUMMARY OF INVENTION

To keep the surgical site infection-free, an antibiotic release system is presented that provides a reservoir of antibiotics attached to the surgical implant that is capable of being released from the surgical implant when ultrasound is applied to the area. This system will be used to ensure that infection is less able to take hold, preventing patient complications, pain and suffering. The present device will reduce and seek to prevent establishment of infection and lower infection rates by maintaining supra-therapeutic antibiotic concentrations at the hardware site during the peri-operative period.

This proposed treatment to lower the incidence of these infections is to localize and release supra-therapeutic levels of complementary antibiotics. Noninvasive Ultrasound (US)-triggered acoustic streaming ensures that the antibiotic load is rapidly disseminated around the implant hardware to achieve the high antibiotic levels that eradicate implant-adherent contaminants and biofilms; staged release from additional sheaths can augment levels in spinal hardware as the previous dose wanes. Through this rapid release of supra-therapeutic levels of antibiotics, while the patient is still in a hospital setting (i.e., within 7 days with no long term retention of antibiotics), spinal infection rates will be significantly decreased and bacterial resistance due to exposure to sub-therapeutic antibiotic levels will be limited. The advantage of the disclosed methods over the current practice is that antibiotic is released post removal of aseptic drains so no drug will leak out through these conduits. Furthermore, the application of ultrasound is completely non-invasive (unlike injection), so it does not require breaching the post-operative site and will not contribute to patient suffering. Not only will the application of ultrasound rupture the PLA membrane and release the drug into the wound site, but the application of ultrasound will also mobilize adherent bacteria making them more susceptible to antibiotics. This two-pronged attack makes ultrasound an ideal tool for drug-delivery to combat surgical site infection.

In a preferred embodiment, a medical device is directed towards a spinal fusion rod comprising an attached sealed reservoir component; wherein said reservoir component utilizes a porous sheath that surrounds the spinal rod which is further covered with polylactic acid (PLA); wherein the PLA that coats the reservoir is capable of being ruptured via ultrasound waves so as to release the contents of the reservoir surrounding the spinal rod.

Further methods utilize other readily ruptured, non-porous, degradable membranes including the aforementioned PLA, but also include poly(vinyl) alcohols or other biopolymers.

A method for treatment of infection at a surgical site comprising: performing a surgical procedure involving a device to be inserted into the body, wherein said device comprises at least one porous polyether ether ketone sheath that surrounds at least a portion of the device whereby a reservoir is created; wherein said porous polyether ether ketone sheath is further coated with polylactic acid covering and wherein said reservoir is filled with a pharmaceutical composition; and applying ultrasound waves to the site of the surgical procedure, wherein said ultrasound waves are sufficient to rupture the porous polyether ether ketone sheath, wherein said pharmaceutical composition is thereafter released from said sheath to the surgical site.

Further embodiments include the use of any suitable polymer or metal material that forms a reservoir, wherein said reservoir is sealed with a biodegradable coating that is stable for at least 7-day; wherein said coating can be ruptured by generation of a mechanical wave.

Further embodiments include wherein the mechanical wave is created via ultrasound, Doppler, or the like. Further embodiments include non-mechanical waves, including IR, radiotherapy, etc.

In further embodiments, reservoirs are suitable for application in stems on orthopaedic joint implants that could be coated and released in similar ways, or reservoirs in spinal hardware (such as the spinal rod itself).

In further embodiments, reservoirs are provided adhered to sutures, staples, pins, rods, fracture stabilization components, indwelling devices such as pacemakers, infusion pumps and other components that are intended to remain in the body, biocompatible polymers, implantable filled components (such as breast implants, and similar body augmenting implants), wherein the reservoir can suitably be ruptured to prevent peri-operative infection.

In further embodiments, the reservoir may be filled with powdered or liquid antibiotics. However, using suitable components, the reservoir(s) may also be filled with and release osteogenic, non-toxic factors or metabolites, such as ascorbate to increase bone formation, parathyroid hormone, peptides, peptoids, NSAIDs, analgesics (for pain control locally for the first seven days) or even local chemotherapeutics after implantation in a stabilization mode.

In a further embodiment, an implantable medical device comprising a polymer material formed around at least a portion of the implantable medical device, wherein the polymer material forms a reservoir attached to or around the implantable medical device, and wherein the reservoir is sealed with a biocompatible coating; wherein the biocompatible coating is stable for at least 7-day post implantation into a body, and can be mechanically ruptured by generation of a mechanical wave. In certain applications, the medical device is applied to the stem on orthopedic joint implants, a spinal rod, or an indwelling medical device. Furthermore, certain embodiments utilized at least one antibiotic in the reservoir, and/or wherein the reservoir contains at least one osteogenic, non-toxic factor or metabolite, such as ascorbate to increase bone formation, parathyroid hormone, peptides, peptoids, NSAIDs, analgesics (for pain control locally for the first seven days) or even local chemotherapeutics after implantation in a stabilization mode.

A further embodiment is an implantable medical device comprising a sheath formed of a polymer material, secured to at least a portion of the implantable medical device, wherein the sheath forms a reservoir attached to or around the implantable medical device, and wherein the reservoir is sealed with a biocompatible pressure responsive coating; wherein the biocompatible coating is stable for at least 7-day post implantation into a body, and can be mechanically ruptured by application of an exterior pressure generating force. In certain embodiments, the implantable medical device further comprising a second sheath secured to a second portion of the implantable medical device, wherein the second sheath comprises a reservoir sealed with a biocompatible pressure responsive coating having a different release profile from the first biocompatible pressure responsive coating. In certain embodiments, said polymer material is PEEK and said biocompatible pressure responsive coating is PLA and wherein said reservoir is filled with a therapeutic selected from the group consisting of: an antibiotic, anti-viral, pain medication, growth factor, anti-fungal, antimycobacteria chemotherapeutic, or combinations thereof.

BRIEF DESCRIPTION OF THE DRAWINGS

FIG. 3 shows one iteration of the Porous (PEEK) reservoir from above (A) and the Porous (PEEK) pore structure (B) by SEM. Bar=300 µm.

FIG. 4 shows a few perspectives of the reservoir. (A) Shows an example of the single pore reservoir (B), a 3-D reconstruction by ρCT of the reservoir, (C) a single pore reservoir (7.5 mm tall, 10.3 mm diam, with 2.8 mm radius bore for spinal rod), and (D) a cross-section by ρCT of the reservoir.

DETAILED DESCRIPTION OF THE DRAWINGS

Figure 1:
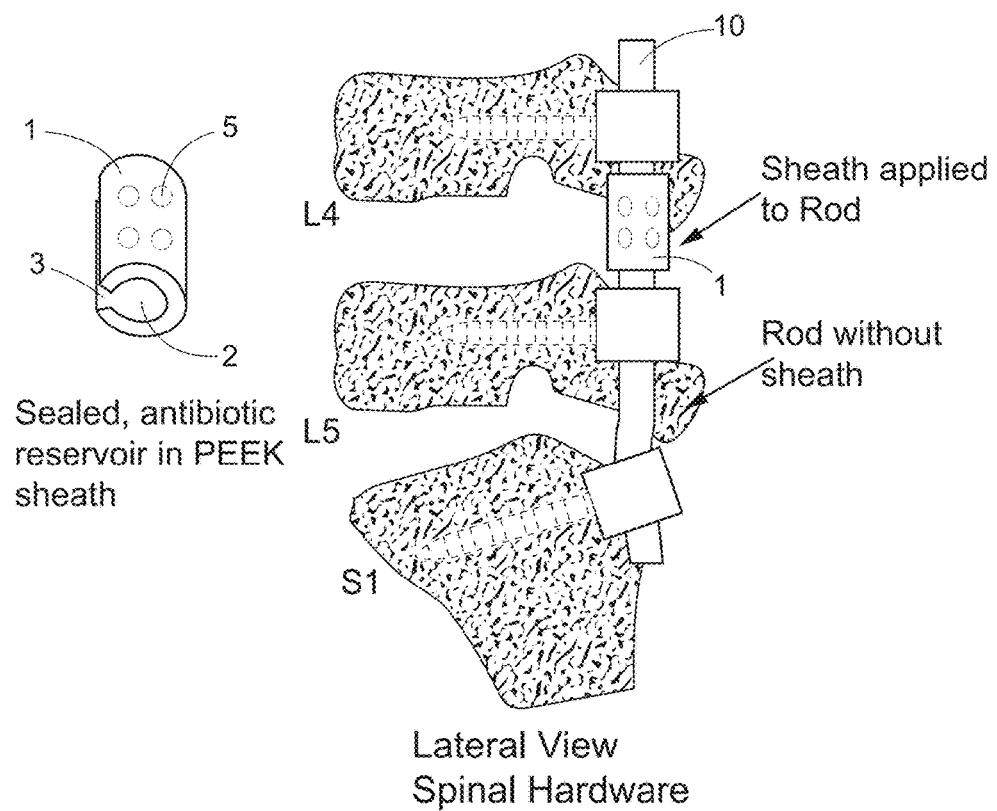
FIG. 1 shows a sealed antibiotic-PEEK reservoir as placed on the vertebral rod. Ultrasound (US) will be applied to trigger antibiotic release.

The approach detailed in this application ensures eradication of pathogens in the immediate post-operative period. The concept and impetus has arisen through the efforts of a spinal surgeon, ultrasound physicist, basic scientist (implant infections), and biomaterials engineering (PEEK and implant retrieval and analysis). It directly addresses the problem of spinal implant infections using innovative applications of proven materials that can quickly and effectively be translated to the clinical arena. This therapy will further lower infection rates and ameliorate the pain, suffering, disability, morbidity, and mortality associated with infections that occur after spinal surgery. The sheath is versatile and, because of its triggered release, ensures surgical site sterilization and increasing device safety. Such supplemental aggressive prophylaxis will greatly improve the outcomes of spinal surgery, especially in the presence of polytrauma and other co-morbidities. This infection-free fusion will diminish the pain, suffering, and extended disabilities associated with these serious surgeries.

A major problem in current surgical settings is the presence of aseptic drains, which ensure depletion of vancomycin (VAN) placed at the surgical site within 48 hrs. The devices and methods described herein allow additional aggressive prophylaxis by augmenting the initial VAN prophylaxis using a novel, pressure/wave triggered, and therapeutic release system tailored for spinal hardware. Preferred embodiments utilize VAN, or a combination of antibiotics that can be augmented to supra-therapeutic levels from a reservoir within a spinal sheath so as to eradicate surviving bacteria, prevent resistance and markedly decrease spinal infection rates. Based on studies, supra-therapeutic antibiotic concentrations at the hardware site during the peri-operative period will reduce or prevent establishment of infection and lower infection rates.

In preferred embodiments, in addition to VAN, other therapeutic bioactive agents can be effectively administered to the surgical site and delivered via the release system. The specific bioactive agent can be tailored based on the individual needs of the patient. Therefore, description of VAN or other antibiotic can be effectively replaced with an appropriate bioactive agent where appropriate in this disclosure. These include, but are not limited to suitable antibiotics, combinations of antibiotics, anti-viral, pain medications, growth factors, anti-fungal, antimycobacteria chemotherapeutics, or combinations thereof.

Accordingly, in one embodiment, the therapeutic clip uses a simple porous polyether ether ketone (PEEK) sheath that surrounds a surgical device such as a spinal rod and releases its contents—mg quantities of one or more combination of antibiotics—upon application of ultrasound. The device functions so that all antibiotics will be released from sheaths during the peri-operative period to ensure aggressive prophylaxis. Use of antibiotic combinations is expected to minimize antibiotic resistant pathogens and to ensure that all contaminating pathogens are eradicated. Preferable bolus release provides for release of more than 75% of the components in the reservoir 24 hours after US. In further embodiments, release of more than 90%, 95%, or of 99% is preferable, to ensure supratherapeutic levels of components are released to the surgical site.

The approach detailed ensures eradication of pathogens in the immediate post-operative period, or can be tailored to a specific medical or biological application as appropriate. The concept and impetus has arisen through the efforts of a spinal surgeon, US physicist, basic scientist (implant infections), and biomaterials engineer (PEEK and implant retrieval and analysis). It directly addresses the problem of spinal implant infections using innovative applications of proven materials that upon completion of this project can quickly and effectively be translated to the clinical arena. This therapy will further lower infection rates and ameliorate the pain, suffering, disability, and mortality associated with infections that occur after spinal surgery.

Prevention of spinal infection depends on minimizing surgical time, stringent sterile measures to minimize bacterial bioburden, immune surveillance, and antibiotic prophylaxis. Hardware is rapidly coated with serum proteins that facilitate bacterial adhesion and antibiotic recalcitrance, while immune surveillance is subverted by bacterial adherence and implant presence[19]. Antibiotic prophylaxis is crucial although the regimen remains controversial[1-3]. In vitro studies show that short, high VAN levels (1 hr., 100× minimum inhibitory concentration (MIC)) reduce bacterial colonization many-fold[9,20] (FIG. 2); this is in keeping with spinal surgeons' use of powdered VAN. Accordingly, a bolus dose to provide suitable antibiotic levels at the surgical site is advantageous.

In the broadest sense, the device is a clip having a reservoir that can be suitably loaded with a therapeutic material, and wherein the reservoir is coated with a pressure responsive material. For example, PLA is one preferred coating that provides for suitable duration (about 7 days before it ruptures in the body), but is easily ruptured through application of ultrasound. Upon application of ultrasound, the membrane ruptures and the therapeutic is expelled from the reservoir in a bolus dose. As described herein, there are several iterations of what the clip is made of, what drug you use, and the type of membrane you cover it with. The modifications depend on the ultimate goal of the clip, namely the amount of material to be released, the time/duration for release after insertion, the ability to use a single or multiple US frequencies for multiple releases from one or more clips, etc. These modifications can be made based upon the variations both described herein, as well as by those of ordinary skill in the art in view of the disclosures provided herein.

As depicted in FIG. 1, a clip device 1 is a sheath which attaches to a 5.5 mm spinal fusion rod 10 during the time of surgery. In the simplest form, the device 1 comprises a porous polyether ether ketone (PEEK) sheath that surrounds an insertable medical component (fusion rod 10) and is engineered to contain a single reservoir 7 with one or more pores 5. This reservoir 7 is filled with powdered, liquid, or emulsified antibiotic and releases its contents—mg quantities of a combination of antibiotics—upon application of ultrasound.

In certain preferred embodiments, the PEEK reservoir is coated with PolyLactic Acid (PLA) to create a rupture profile upon application of ultrasound. In other embodiments, the membrane that forms the reservoir is made up of any suitable material that enables release through application of US or other pressure generating application. In further embodiments, membranes may also be ruptured through IR, electric fields, a pressure jump, temperature jump, or other known energy applications suitable to initiate release. Suitable materials thus may be biodegradable or non-biodegradable biocompatible polymer such as PLLA, PCL or other suitable materials known in the art.

The sheath can be manufactured by selective laser sintering (SLS), or by injection molding and in its simplest embodiment is comprised of poly (ether ether ketone). In a preferred embodiment, the sheath will be attached to a spinal fusion rod at the time of surgery. Accordingly the sheath is implanted into the surgical site, wherein the sheath contains the reservoir full of antibiotic. A particular feature of the PLA coated clip is that it can be ruptured using US, which allows the reservoir to be stable until rupture is desired (within the first 7 days).

Figure 2:
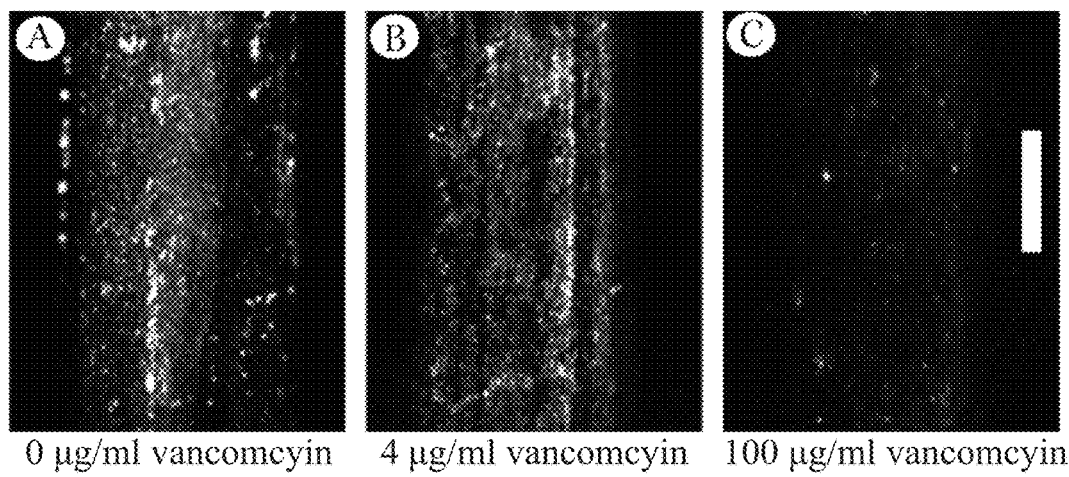
FIG. 2 shows the bacteria (*S. aureus*) rapidly adhering to the metal surfaces, in the presence of low levels of VAN. At 100×MIC. Significantly decreasing left to right, as fewer bacteria adhere to the surfaces (Magnification: bar=200 $\mu m^9$).

Approximately four-seven days post-implantation, ultrasound will be delivered to the wound site with a standard clinical probe. This will rupture the PLA membrane and release the antibiotic into the surgical site. US is chosen for drug release as (1) the energy is sufficient to produce mechanical waves that disrupt the thin polymer films encasing the drug, and (2) US decreases bacterial adherence (by ~100× at 20 min) and, in the presence of VAN, further decreases bacterial numbers by 50-90%[23-28]. The combination of antibiotics will eliminate any contaminating bacteria before they develop into a full-blown infection. For example, FIG. 2 depicts three images showing 0 ug/ml of VAN, 4 ug/ml of VAN or 100 ug/ml of VAN and the lack of white in FIG. 2C indicates a massive reduction in bacterial levels as compared to FIGS. 2A and 2B. To reach these levels, greater than 90% of the encapsulated antibiotics will be released from sheaths during the peri-operative period to ensure aggressive prophylaxis. The appropriate bolus dose can be determined by one of ordinary skill in the art. Use of antibiotic combinations is expected to minimize antibiotic resistant pathogens and to ensure that all contaminating pathogens are eradicated. The short duration and high levels of antibiotics should minimize development of antibiotic resistance.

In one iteration, the sheath is manufactured of PEEK. PEEK is a bioinert polymer that has been used successfully[21] in spinal rods, screws, and fusion cages and can be molded or patterned[22]; this moldability is critical for the desired geometries (FIGS. 3, 4). In further embodiments, the sheath may be replaced by a different biocompatible material, for example, a non-limiting list including materials such as PLAGA, polyvinylalcohol, epsilon-carproic acid, etc. These materials are often understood to be biocompatible, biodegradable polymers so that the clips will degrade over time (after the release of the antibiotics). Indeed, other suitable biocompatible and biodegradable materials are known to one of ordinary skill in the art.

VAN is active against Gram-positive pathogens including MRSA. Additional antibiotics can be combined with VAN so as to provide both Gram-negative and some Gram-positive coverage including but not limited to: tobramycin (TOB), cefazolin (CFZ), daptomycin (DAP), aztreonam (ATM) and ciprofloxacin (CIP), and combinations thereof. In a typical scenario, VAN is applied prophylactically to the surgical site. As VAN levels wane, post-op, US triggering of the reservoir antibiotic prophylaxis system broadens antimicrobial coverage and provides for increase of antibiotic levels at the surgical site.

With particular regard to the reservoir sheath, delivery channels in the polymer surfaces connect the reservoir to the surface and are sealed with a poly(lactic acid) (PLA) membrane. All sheaths will be loaded with antibiotics (ABX=VAN+: TOB, CFZ, DAP. ATM or CIP), or other suitable antibiotics, combinations of antibiotics, anti-viral, pain medications, growth factors, anti-fungal, antimycobacteria chemotherapeutics, or combinations thereof. Reservoir stability and antibiotic release profiles can be tuned based on the time of ultrasound insonation, the thickness of the coating, the energy and frequency of the insonation, and the number of pores in the reservoir.

The antibiotic-loaded sheath provides for stability to flexion, stable association and minimizes generation of wear debris so that surface integrity is maintained over time. However, US release of the antibiotics contained within the reservoir provide for effective treatment and reduction of *Staphylococcus aureus* (*S. aureus*), methicillin-resistant *S. aureus* (MRSA), *Staphylococcus epidermidis* (*S. epidermidis*), the most common pathogens in deep infection[29] and other common Gram positive and Gram negative pathogens found in infection.

Furthermore, the antibiotics released from the reservoir show efficacy regarding eradication of planktonic (non-adherent) and biofilm formation on adjacent hardware. Accordingly, augmenting the waning VAN with prophylactic antibiotic combinations, or other suitable antibiotics are effective in reducing and eradicating Gram-negative AND Gram-positive pathogens so as to significantly lower spinal infection rates.

In certain embodiments, it is also suitable and advantageous to utilize microcapsules within the reservoir. In this sense, a solid or liquid therapeutic material may comprise a portion of the reservoir and suitable microcapsules intermixed therein. Encapsulated may be any number of therapeutic materials, or even the same material as in the remaining portion of the reservoir. However, the microcapsules are made of a suitable material that will rupture, preferably after they are released from the reservoir. The material can then be further ruptured by a different frequency application, or may even biodegrade once in the body cavity. Suitable materials are known to one of ordinary skill in the art through the use of suitable microcapsules. This application will allow the microcapsules to spread away from the reservoir to then, upon release, provide for therapeutic application of the encapsulated material to the wound site.

For example, that may allow for addition antibiotic duration, different antibiotic application, or application of other materials as previously described as suitable for placing in the reservoir.

FIG. 3 depicts a suitable porous device, wherein the pores 6 provide for many different openings for material to be stored and also released. A detail of this is depicted in FIG. 3B. The porous material is covered in a suitable pressure responsive material that upon rupture, allows for material to leave these pores into the body at a different rate than using one, two, three, four, five-ten, or more openings as is defined in other embodiments. Similarly, the size of the openings can be modified in certain embodiments (e.g. FIG. 7), to allow for modification of release rates.

Figure 9:
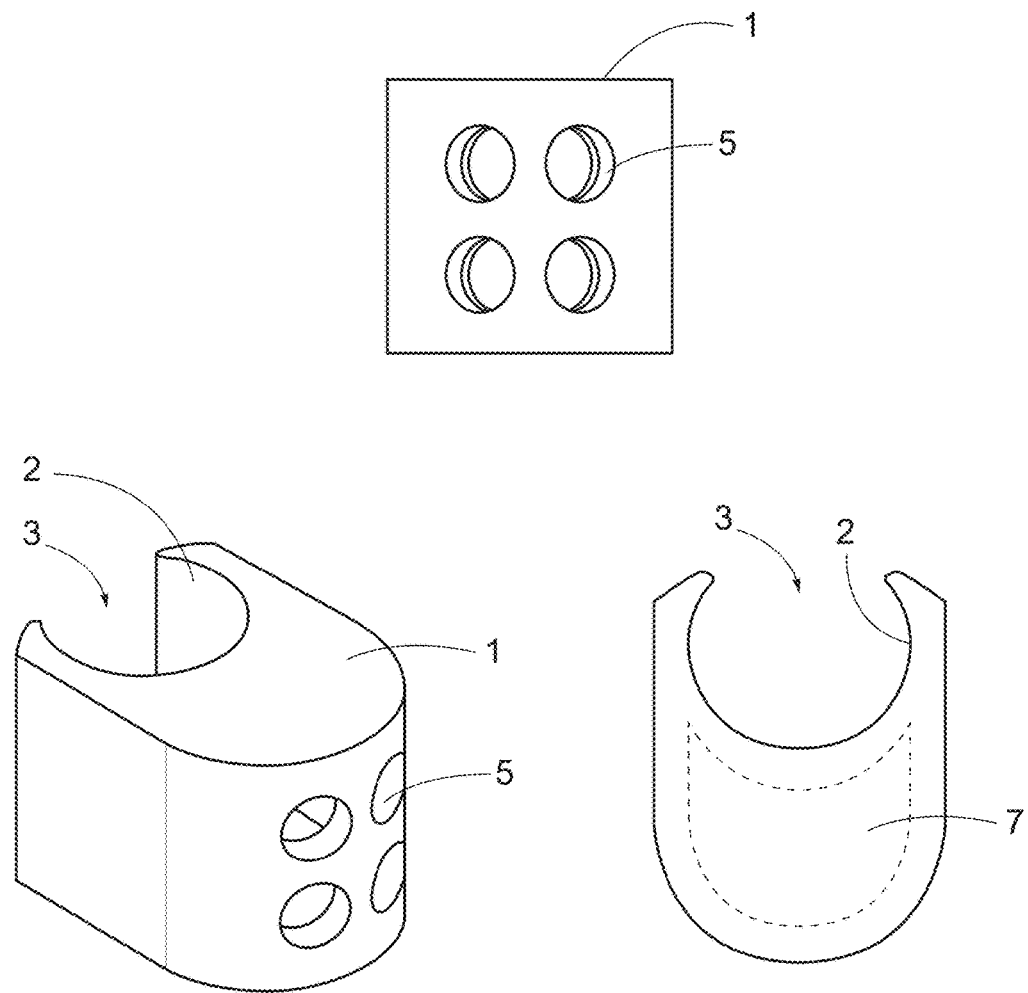
FIG. 9 depicts a detail of a clip having a reservoir and four 2 mm openings for insertion and release of therapeutic materials.

FIG. 4 depicts one embodiment of the clip 1 having a single release pore 5, a recess opening 3 and concave recess 2 disposed along the longitudinal axis of the clip, so as to provide a feature suitable for attachment to a rod. The dimensions of the opening 3 and the concave recess 2 can be modified based upon the size of the rod or shape that the clip is being attached to. As many of these materials come in a standard size (i.e. standard diameter rods), clips can be manufactured to be compatible with these standards sizes. A reservoir 7 is depicted in the clip on FIG. 4D (a cross-sectional image) wherein pharmaceutical materials can be loaded into the reservoir and then coated with the pressure responsive material. FIG. 9 provides a further detailed example of variations of the sheath device 1 depicting the release pores 5, the concave recess 2, and the reservoir 7.

Figure 5:
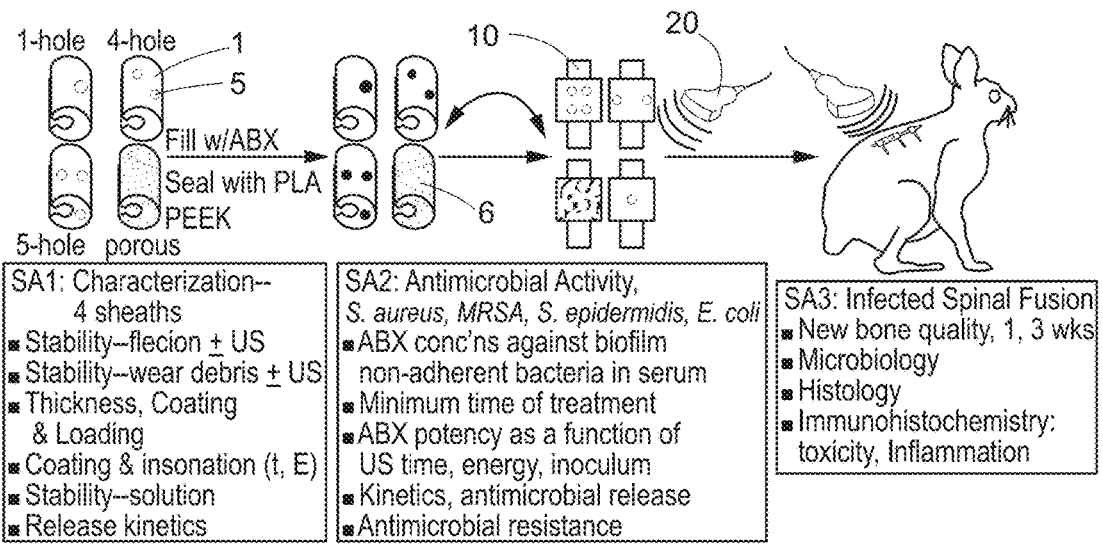
FIG. 5 shows a view of the experimental plan with the four different sheaths carried through until the in vivo experiments.

FIG. 5 further depicts several embodiments of clips, including a clip having t-hole, 4-holes, 5-holes, and a porous clip. These are merely non-limiting examples, as the clips can be manufactured to have an appropriate number of openings as necessary and suitable for the proper release profile.

Figure 7:
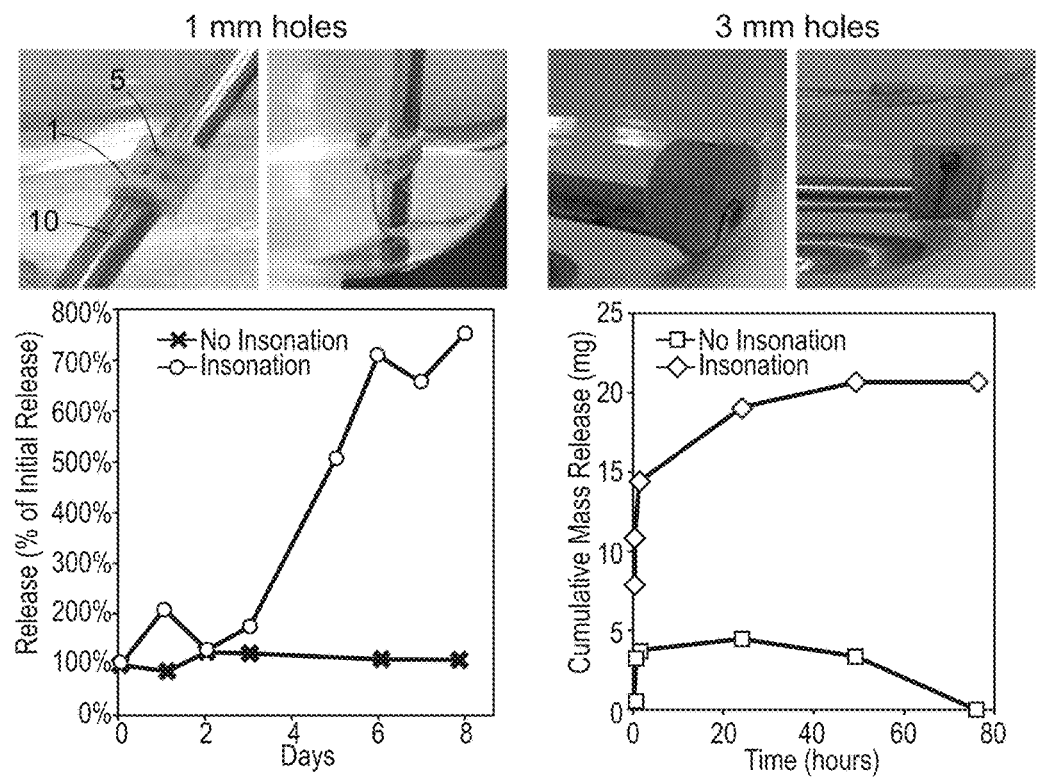
FIG. 7 shows the release of antibiotics from PLA-coated PEEK reservoirs. Multiple 1 mm holes (left) and one 3 mm hole (right) sheaths were submerged in water and release of methylene blue (MeB) or MeB+VAN was measured spectrophotometrically.

As depicted in FIG. 7, unlike classic release systems[30], the spinal sheath is designed for rapid, triggered, bulk release (bolus release) of high levels of antibiotics that have complementary activities to increase efficacy in sterilizing post-surgical sites. Thus, after depletion of surgically-placed VAN, US insonation will release VAN (inhibits cell wall cross-linking)+TOB (protein synthesis inhibitor), VAN+ CFZ (inhibits cell wall synthesis), or VAN+CIP (inhibits DNA gyrase) from the sheath. This bolus dose of one or more therapeutics will treat the area around the surgical site, and remove some issues with systemic administration of these therapeutics. Indeed, the ability to provide therapeutics such as pain medications, wherein systemic dosing may require higher doses, allows customization of the device based upon release profiles to release appropriate therapeutic materials to the surgical site.

In preferred embodiments, the sheath (clip), is inserted during a surgical procedure. In the case of a spinal fusion, the wound and surgical site is provided with high levels of antibiotics and a drain. The drains are removed at between 1-7 days post-surgery. After the removal of the drains, US or other means are applied to the wound site and the biocompatible polymer coating is ruptured to release the contents of the reservoir. Therefore, an appropriate method of treatment provides for insertion of a clip having a reservoir and reservoir openings, and a suitable pharmaceutical material for treatment of a patient in said opening and a biocompatible pressure responsive material coating the reservoir opening; applying a force to rupture the biocompatible polymer thereby releasing the contents of the reservoir into the body for treatment.

In the broadest applications, the material of the clip is a biocompatible material suitable for attachment to a surgical site. The clip possessing a reservoir and opening to said reservoir so that a therapeutic material can be placed in the reservoir. The clip is preferably then coated or dipped in a pressure responsive biocompatible coating material that will rupture upon application of an exterior force to the biocompatible coating material, for example US. The therapeutic material, as described herein may be an antibiotic, a combination of antibiotics, or other suitable therapeutic materials as determined by one of ordinary skill in the art. The rupture profile of the biocompatible coating material is such that rupture by US or other external force is typically performed within about 7 days post-surgery.

Experimental Design

To Characterize the Stability, and Release Kinetics of an US-Activated Antimicrobial Release System The spinal sheath device as described in the embodiments therein is a new, triggered antibiotic release system that clips onto existing spinal rods. The US-triggered, bulk antibiotic release system, the novel sheath design that uses approved materials, and the triggering of aggressive spinal antibiotic prophylaxis after removal of spinal drains are all novel as neither bulk release systems nor controlled release systems are available for the spine. Adding to the novelty, more than one sheath could be used for additional staged antibiotic prophylaxis (within the targeted 7 day window) or for the release of osteogenic or analgesic factors. Use of therapeutic US for drug release brings the added advantage that it can occur locally at the physician's direction, and when antimicrobial, will disrupt biofilms, facilitating antibiotic effectiveness. Importantly, by decreasing spinal infection rates, this system will ensure that fewer patients endure the disability associated with establishment of spinal infection.

The significance of this approach is relative in addressing intractable back pain or in the event spinal stability is threatened through trauma, as fusion may be necessary. Infection is a significant surgical risk[11, 12] and infection-associated osteolysis compromises healing and even more crucially, spinal stability. Antibiotic treatments and, at times, further surgery are required. If the infection is recalcitrant, increased morbidity is likely[13-15]. New, nosocomial and hospital-acquired resistant bacterial strains further compromise patient health. This local, prophylactic treatment using non-invasive US to trigger bulk release of supra-therapeutic doses of antibiotics through disruption of a PLA-coated PEEK reservoir can satisfy this critical need to significantly lower spinal infection rates, facilitate infection-free fusion, and decrease the immense costs and psychosocial impacts of these infections.

The design of the polymer sheath (clip) 1 (FIGS. 1, 4A-4D) allows placement on the spinal rod 10 between spinal screws so as to not affect hardware function; the sheath will remain on the hardware and will be tested/modified for this stable association. Four sheaths of varying porosity will be refined to achieve our goal of >99% elution within 24 hrs. To ensure that drug release occurs at the appropriate time, the drug reservoir is sealed with PLA[34, 35]. Rupture of the PLA coating on the sheath occurs because of US stimulation of the air within the pores; these same streaming effects cause rapid ejection of the reservoir antibiotics. Thus, application of US disrupts the PLA, loosens adherent bacteria[36, 37], and disperses antibiotics around the sheath onto the adjacent hardware surface and into the tissue and dead space.

Because antibiotic resistance is fostered by exposure to low/sub-MIC antibiotic levels, release will be tailored to drop levels not expected to foster resistance, that is to <0.1×MIC within 24 hrs. In preliminary experiments, the following were tested: (1) US release of loaded VAN (10 mg in a porous (approximates that of trabecular bone), PLA-sealed PEEK block and showed 7.5 mg of released VAN after 10 min US insonation (5 MHz, 4 MPa). (2) US-mediated methylene blue (MeB) release from a PLA-sealed multiport (1 mm) PEEK sheath (FIG. 7, left). The non-insolated controls increased MeB release by 26% at 2 days, with no additional release out to 6 days. The US insolated group increased MeB release by 757% over 8-days[38]. (3) Release after US-rupture of PLA coating using a one-hole (3 mm) sheath (FIG. 7, right) loaded with 50 mg VAN and 5 mg MeB. During the first 15 min of immersion, 11 mg and 3 mg of drug were released (due to surface amounts in PLA) from the groups. No additional drug leeched from the control sheath. With a 15 min insonation (5 MHz, 3 MPa), 15 mg was released within one hour and the remaining 24 mg of drug was released by 72 hrs[39]. (4) Three PLA coatings for US rupture using highly porous PEEK.

Sheaths were submerged 5 or 10 times in 50 mg/ml PLA/CHCl$_3$ (75-120 kDa; 5-50 or 10-50) or 5 times in 250 mg/ml PLA (5-250), resulting in coatings containing 7.3±1.5 mg, 12.9±0.75 mg or 234±12 mg of PLA, respectively. The 5-250 showed the greatest stability, with the 5-50 leaky and the 10-50 showing stability after an initial release (perhaps due to surface MeB). Upon insonation (30 min, 5 MHz, 3 MPa$_{peak-peak}$), the 5-50 showed a 10× increase in release, the 10-50 and ~5-250 showed ~5× increase. Finally, integrity of the sheaths to long-term flexion, both before and after insonation, as well as their surface integrity and production of wear debris will be tested and PLA coating adjusted to insure >7 d coating stability and long-term sheath stability. Importantly, the sheaths will not be weight-bearing so that these tests model the most extreme conditions ensuring that no debris or loosening will arise during use of the sheath.

Figure 6:
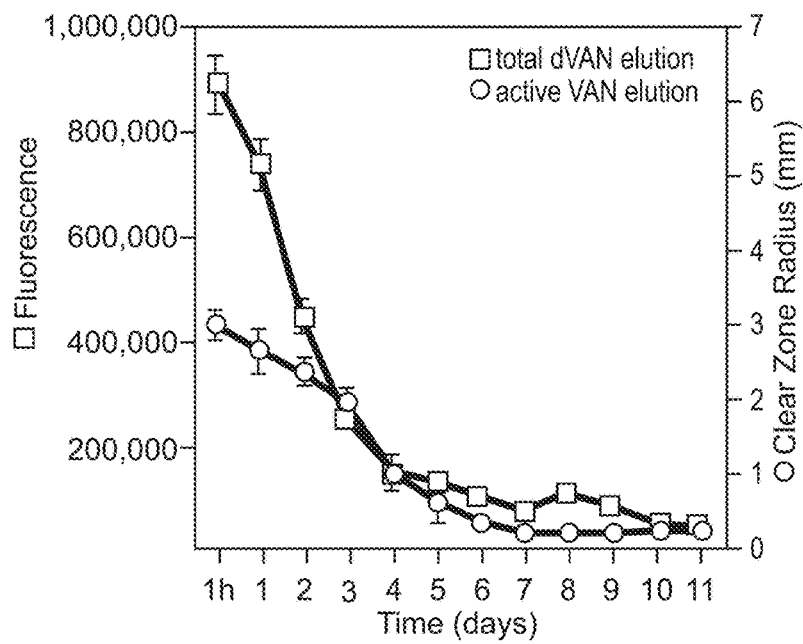
FIG. 6 shows the passive antibiotic elution from trabecular bone as measured by elution of dansylated vancomycin (dVAN) and by zones of inhibition (bottom panel) in a bacterial lawn. Antibacterial activity of bone allografts: comparison of a new vancomycin-tethered allograft with allograft loaded with adsorbed vancomycin. This is an example of the elution that can be achieved without enhancement by ultrasound.
Figure 6:
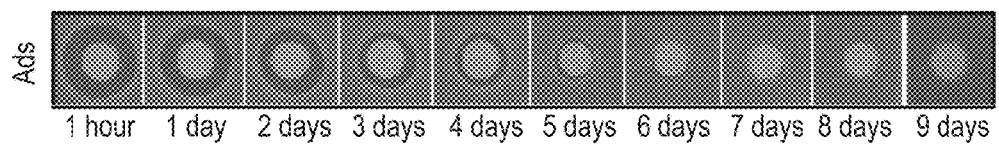

To model the sheath, VAN was loaded in allograft bone and saw rapid passive elution and significant bacterial killing, especially within the first 48 hr. (initial loading: 10 mg/ml VAN, FIG. 6). However, a preferred sheath is sealed so that it retains antibiotics without leakage for up to 7 days (to allow for triggered release at any time prior to patient discharge) and then releases >99% of the antibiotics within 24 hrs. of US insonation. Accordingly, release can be determined based on the specific needs of the patient. Therapeutic materials loaded into the sheath may be liquids, solids, gels, or combinations thereof. Release profile of these different materials may require different structures to allow for the appropriate release.

Test PEEK sheaths were fabricated by the Drexel/Invibio partnership and sterilized by autoclaving. To test appropriate PEEK sheaths, several tests are performed to monitor sheath loading and release using a 2.5 mg/ml MeB solution. Loaded PEEK will be sealed by immersion in ~5-25% (w/v) PLA (60 or 75 kDa) in chloroform. Dipping will be performed 1-10 times to vary PLA thickness so that coatings are stable for >7 d (tested to 2 wks) and can be reproducibly ruptured by the US mechanical pressure wave.

ABX retention and release conditions will be modeled on MeB results. ABX will be loaded in pH 6.0 NH$_4$OAc[40-43] to allow drying without a salt residue; alternately, ABX will be inserted as a slurry to favor powdered ABX. ABX release will be determined by spectrophotometry (CFZ, $\lambda$=254 nm) or ELISA (VAN, TOB, CIP). With insonation, it is preferred to achieve between about 1000-5000×MIC (1-5 mg/ml; for a 5 cc dead space).

To measure any residual ABX release, the "emptied" composite will be bathed in fluid for an additional 1-6 days and ABX release monitored as above. ABX loading and US parameters will be tailored so that residual elution is below 0.1×MIC/24 hrs. (to minimize selective pressure that could favor antibiotic resistance). Sheaths will undergo mechanical testing for coating and sheath stability to insure long-term integrity and retention on the spinal rod. Stability to insertion and dynamic flexion tests will be measured while clipped onto lumbar fusion rods as per ASTM standard test method for spinal implant constructs in a vertebrectomy model (ASTM F1717-12a). Generation of wear debris will be assessed by collecting wear particles on filters[21]. Coating thickness will be determined by FTIR microscopy and surface integrity will be measured before and after insonation by SEM.

Loading of ABX into the porous PEEK surface: Four PEEK sheaths will initially be tested: 1. PEEK with the porosity of trabecular bone; a single reservoir PEEK sheath with 2. One hole (3 mm). 3. Four holes (3 mm) or 4. Five holes (3 mm). FIG. 5 and FIG. 7 each depict certain embodiments and variations of the clips. MeB (2.5 mg/ml solution in 0.025 M NH$_4$OAc) will be loaded and lyophilized to yield a blue construct. All ABX will be dissolved in NH$_4$OAc, pH 6.0. Equal weights of ABX (VAN+TOB, VAN+CFZ, VAN+CIP) will be dissolved and repeated solvent evaporation used to reach ~5-25 mg of each (1-5 mg/mL). Additional geometries of the holes are possible to achieve the desired release kinetics, for example as depicted in FIGS. 5 and 7.

Elution from PEEK: Total loaded and eluted amounts will be determined for each compound. MeB and CFZ will be determined spectrophotometrically. VAN, CIP, and TOB will be determined by ELISA (VAN: Emit 2000 (Beckman Coulter), TOB: (Reagan ELISA kit), TOB: CEDIA Tobramycin II assay, Fisher Sci). Amounts of active antibiotic will be determined using disk diffusion assays compared to control ABX amounts.

Application of the PLA coating: The MeB/ABX-loaded sheath will be dipped into sterile 5-25% (w/v) 60 or 75 kDa PLA (Lakeshore Biomaterials, Birmingham Ala.) in chloroform or other suitable solvent. This solvent will be removed by evaporation and dipping repeated 1-10× to increase coating thickness; polymer viscosity can be adjusted through adjusting PLA concentrations or MW. Adjustments of the PLA concentration and thickness can modify the release profile of the reservoir. Accordingly, several different reservoirs having different PLA concentrations or thicknesses results in reservoirs that can be released under different conditions.

Stability of spinal sheaths over time: The MeB-containing PLA sealed constructs will be incubated in 3 ml of PBS, 37° C., under static conditions or using a rotary platform for mixing. Bathing fluid will be replaced and analyzed spectrophotometrically ($\lambda$=665 nm; $\varepsilon$~70,000 M$^{-1}$ cm$^{-1}$ [44]) for methylene blue leakage at 2, 6, 24 hrs. and then daily for two weeks. Bathing fluid from MeB-free PLA-PEEK will be used as a negative control and known amounts of MeB as a positive control.

Insonation of Spinal Sheaths: US parameters for MeB or ABX release at 37° C. will be established by varying single element transducer frequencies (500 Hz to 5.0 MHz) and the output levels (0.5 MPa to 3 MPa peak negative pressure; i.e., from well within the FDA limits for diagnostic US to high intensity focused US; HIFU) pressure waves. Other US parameters to be varied include duty cycle (from 100% or continuous to 20%), duration of insonation (1 to 30 min) and number of repeat exposures (1 to 3). The parameters for US rupture are modified based on the particular release profile of the sheath.

Flexion Testing: Sheath attached to a spinal fusion rod will be subjected to a compression bending fatigue test per ATSM Standard F1717-12a using an electrodynamic mechanical testing system (MTS Acumen, MTS Systems Corporation, Eden Prairie, Minn.). The rod will be loaded at 5 Hz for 5 million cycles at 75% of the compression bending strength. The sheath attachment strength before and after loading will be assessed via a pull-off test. The integrity of the sheath coating before and after loading will be assessed under SEM.

PLA Layer Thickness: PLA film thicknesses will be measured after sectioning using a microtome (Leica SM2400, Leica Microsystems, Wetzlar, Germany), by FTIR microscopy (Nicolet iN10MX, Thermo Fisher Scientific, Waltham, Mass.).

In-vitro wear particle analysis: Following flexion testing, insonation, or both, wear particles from polymer sheaths will be isolated in saline and analyzed following ASTM F1877-05e: Standard Practice for Characterization of Particles[45]. Aliquots of the saline media will be filtered through polycarbonate membranes with pore sizes of 1, 0.1, 0.05, and 0.01 µm, imaged by Environmental Scanning Electron Microscopy (ESEM) and analyzed for the presence of PEEK wear particles.

Scanning Electron Microscopy (SK): A FEI XL30 Scanning Electron Microscope (SEM, Drexel's Central Research Facilities) will be used to obtain images of surface integrity of polymer samples at various stages of antibiotic and methylene blue retention and when colonized by bacteria. Bacterial samples will be fixed with 4% formaldehyde and undergo staged dehydration with ethanol. All samples will be sputter coated with platinum or gold before imaging.

As developed and tested, the reservoir system provides for a US trigged release of an antibiotic prophylaxis system to supplement surgically-administered VAN. Conditions for ABX retention in the sheath, and conditions that allow rapid release of the ABX upon US insonation require experiments routine in our laboratories.

Importantly, with the 1 hole design, significant release occurs yet the coating remains stable for >7 days. Using the conditions for sealing methylene blue in the sheaths, ABX will be loaded and release kinetics characterized with a goal of >7 days stable retention and >99% antibiotic release after US insonation. It is important to note that the targeted 7 day stability coincides with hospital stays and the content of all sheaths placed by the surgeon will be released during this time so that no long-term retention of ABX occurs.

Modification of the release profile of the sheath can be made through selection of various sheath or coating materials, modification of thickness of the same, to achieve, rapid, ultrasound triggered release of the contents of the reservoir. Based on the studies and preliminary data, PLA coatings described herein are stable to 8 days and can be ruptured to allow rapid release. In certain embodiments, several PLA coats can be applied or higher PLA concentrations or MW could also be used. Accordingly, the modification of the PLA coat or the PEEK sheath, allows for inclusion of more than one reservoir within and surrounding the surgical site. This provides that selective rupture of one or more reservoirs can aid in targeted release of drugs to the surgical site.

It is envisioned that two or more reservoirs can be added to a surgical site, each having different release profiles, therefore allowing a first reservoir to be ruptured at a first time point and a second reservoir to be released at a second time point. Alternatively, two or more reservoirs may contain separate drugs that would otherwise interact or degrade through contact within the reservoir. These can then be ruptured together, or separately, based on the specific interactions. Accordingly, a single clip may contain a single reservoir or more than one reservoir and wherein the reservoirs can be either simultaneously ruptured or independently ruptured as necessary for interaction of the components.

Certainly, it is conceived that two, three, or more reservoirs can be added to the surgical site and provide for release based on needs of the patient to reduce infection. Indeed, such application allows for one or more materials to be released into the surgical site based upon necessary treatment protocols for the particular surgery.

ABX release will be determined spectrophotometrically or by ELISA as a function of coating thickness, insonation time, and energy. Data shows that insonation can rapidly release MeB from PLA-coated porous PEEK, and from PEEK reservoirs, importantly, antibiotics can be rapidly released from reservoirs. By varying US exposure parameters, rapid release rates for the composite samples are achieved[46] as the US wave will cause acoustic radiation forces and cavitation of trapped gas bubbles which will cause a streaming-like effect and aid ABX expulsion.

Certain coatings may require additional release properties, and therefore, a Vitamin E or other emulsion may be further utilized to ensure the presence of air for the US release as well as a readily dispersible formulation for the mixed ABX[47-49].

Further Testing

The polymer-sealed ABX polymer sheaths will be tested in the presence of a Ti wire to mimic their placement on spinal rods and to reproduce the challenges associated with bacterial contamination of unprotected hardware adjacent to the sheath. The Experimental data show that the one-pore device will, with some tuning, achieve the desired release (>99%) over 24 hrs. Several Experiments are included so as to test the efficacy of the reservoir system.

To model antibiotic prophylaxis in the presence of an establishing bacterial contamination, the sheath system will be placed in a solution containing $10^6$-$10^7$ CFU/mL of bacteria; ABX will be released by US insonation upon immersion. To model an established infection, biofilm will be formed on the sheath system over 48 hrs. US insonation will release depot antibiotics and mobilize bacteria Controls without ABX will determine the extent of this US mobilization. Finally, long-term experiments (sampling up to 12 weeks) will be performed with the different ABX sheath systems to monitor changes in ABX sensitivity.

All experiments use *S. aureus* (ATCC®25923™ or AH1710[57]), MRSA (clinical, USA300 strain), *S. epidermidis* (ATCC®155™), and *E. coli* (ATCC®25922™), representative of common organisms encountered in spinal infections[51]. All experiments will test the \ABX\ with US release, VAN alone (as a control and modeling current prophylaxis), US alone, and no antibiotics. The first series of experiments will test bacterial survival ($C_i$~$10^3$-$10^6$ CFU/ml) prior to (t=0 min) and after (t=20 min, 40 min, 1 hr., 3 hrs., 6 hrs., 24 hrs.). US insonation as a function of time and acoustic power (effective range for drug release determined in Specific Aim 1), bacterial strain, and bacterial amount. In a parallel study, biofilm will be formed on the constructs for 48 hr prior to insonation and the ability of the insonated system to eradicate this biofilm will be tested using the timepoints given above. All experiments will be performed in human serum as it models aggregation of bacteria in blood[58]-like fluids, such as wound exudate. Bacterial numbers in serum will be determined after proteinase K digestion to disperse aggregates, and the number of implant- and sheath-adherent bacteria determined by direct counting after suspension from the surface. Antibiotic elution from loaded and emptied sheaths will be monitored over the long term using disc diffusion assays (FIG. 4) until no zones of inhibition are seen. Importantly, drifts in antibiotic sensitivity of the different strains will be determined during exposure to post-insonation sheaths over 12 weeks using broth microdilution assays[59]. A subset of samples will be visualized with confocal laser scanning microscopy or SEM to assess surface distribution of bacteria.

Methods

In experiments with US insonation, focused beams (resulting in higher acoustic pressures in the smaller focal zone) vs un-focused beams (lower pressures dispersed over a larger region) will be used to define conditions which decrease bacterial adherence on adjacent hardware.

Antimicrobial Susceptibility Testing:

Broth microdilution MIC and disc diffusion testing (Kirby-Bauer) will be performed using cation-adjusted MHB according to CLSI methods using the antibiotics eluted from the sheaths. For susceptibility testing, cultures will be maintained in M-IB. Amikacin, azithromycin, carbapenem, levofloxacin, oxacillin, tetracycline, polymixin B and VAN will be used as standard antibiotics and interpretation performed according to CLSI guidelines.

Enumeration of Bacteria:

Bacteria will be cultured and counted using previously published methods[7,9]. Briefly, ~$10^4$ CFU of proliferative bacteria will be incubated with sheaths for 0-48 hrs. in human serum (Sigma), and bacterial number in bathing media determined after dilution and plating onto 3M Petri-Films (Countable range, ~30-800 CPU/film) or after digestion with proteinase K (50 µg/ml for 1 h, 37° C.), followed by dilution and plating. Adherent bacteria will be retrieved by sonication in 0.3% Tween-80[2], followed by dilution and plating.

Biofilm-Sensitivity to Sheaths with US.

Biofilms, using each of the four strains[59], will be formed on the PLA-coated sheaths by incubation in serum, 48 h, 37° C. Antibiotic release will be initiated by insonation (e.g., 1 MHz continuous wave with a P>500 kPa, 20 min). Incubation will then continue for an additional 6-24 hrs. Planktonic and adherent bacteria will be recovered and plated as above Controls include biofilms formed on sheaths with no ABX, sheaths that have not been exposed to US, and sheaths with no ABX and that have not been exposed to US.

Results

These experiments define the efficacy of the antibiotics eluted from the different sheath constructs, as well as sheath and hardware colonization. The results of preliminary data strongly support the ability to achieve the target range of >500×MIC. Because we are using serum, our success criteria are based on measured reductions in bacterial counts in that media at therapeutic antibiotic levels. Importantly, in our studies of antibacterial surfaces, we have noted that even a 10-100 fold reduction in numbers of adherent bacteria, in vitro, translates into real efficacy in vivo[61,62].

Additional strategies could include changes in timing of US (to maintain high ABX levels or purposefully allow them to drop), or altering sheath ABX carbapenem or daptomycin). Each modification provides for opportunities to particularly tailor the release based on the needs of the patient. With respect to toxicity and biocompatibility concerns, in view of the toxicity of VAN, TOB, and CIP towards osteoblastic (MC3T3-E1) and chondrocytic (N1511) cells as a function of dose and time of exposure, VAN showed low toxicity with some cell death initiating above 1 mg/ml; TOB toxicity was at ~0.5 mg/ml, and CIP at 0.15-0.2 mg/ml[63]; DAP and ATM were not determined at that time. Thus, biocompatibility becomes an issue only with large amounts of antibiotic and, with this in mind, the profile and amounts of the total antibiotic amounts will remain in the low mg range for each reservoir. Where CIP proves to be the most effective for certain infections, amounts will have to be carefully tailored to maximize antibacterial effects while minimizing site toxicity. Because exposure is short, this risk is small compared to the risks associated with spinal infection, osteolysis and non-fusion.

In preferred embodiments, certain methods of monitoring 4 strains of bacteria as each is representative of important pathogens in spinal infection and the sheath ABX are expected to show differential selectively. Throughout, methods comprise monitoring acquisition of resistance, both in these experiments and in the animal experiments. Accordingly, the method allows one to minimize exposure to sub-MIC levels of ABX so that selective pressure is not developed.

Finally, key to this aim will be maintaining the adjoining hardware without bacterial contamination. The tests in this specific aim will use US insonation to release the antibiotic AND disrupt bacterial attachment. As noted previously, US insonation can increase the efficacy of antibiotics, presumably by returning the adjacent bacteria to a more "proliferative" state[54], the only state that is susceptible to antibiotics.

To Determine the Utility of the Sheath in Eradicating Infection in an In Vivo Model of Infection.

Infection rates after spinal fusion depend on the surgical approach, indication for surgery (intractable pain, trauma, tumor), and the presence of co-morbidities Early peri-operative wound contamination accounts for the majority of the cases, with late/hematogenous infection accounting for only a small percentage[16,64,65]. The sheaths developed herein aim to aggressively sterilize their surroundings during the peri-operative period when most infection establishes.

The success of the sheath system depends on maintenance and then rupture of the PLA seal with rapid release of ABX. Initial testing of the instrumentation performed in scavenged cadaverous rabbits provides evidence and support for optimization under surgical conditions. Furthermore, the US parameters are optionally tested and determined in conjunction with appropriate sheath systems in the spinal implant infection model. Evaluations in these models include radiographic, histological, μCT, blood levels of antibiotics and bacteria, and microbiological, including typing and antibiotic sensitivity.

In these experiments, one ABX combination will be used that is most effective against adherent and planktonic bacteria as established in the previous aims. μCT will be used to assess the structural properties of the developing spinal fusion, as well as bone quality. Experiments have shown that μCT allows analysis through segmentation of bone density associated with an infected, healing femur[61,67].

Rabbit spinal implant infection model[66] that uses non-contiguous sites to allow the evaluation of multiple spinal sheaths within one animal is used as a model. Several studies on such models were performed wherein a spinal fusion in a pilot study in rabbits using three spinal levels with maintenance of the isolation of the infected sites, Bone quality will be examined for all conditions, however, the purpose of these experiments is to ensure an infection-free environment for spinal fusion without addressing efficacy of US for bone healing.

Experimental Design

The first set of experiments uses rabbit carcasses to establish US parameters that reproducibly release the desired amounts of ABX within a mock spinal fusion site. Preliminary tests on such animals in which VAN-loaded (4 mg), PLA-sealed sheaths were placed in 4 spinal levels of a cadaverous rabbit. Site 1 and Site 3 were inoculated with $10^4$ CFU S. aureus in 100 μL PBS, and Site 2 and 4 were encased in plastic to collect released VAN. Without any optimization of US parameters, ~50% of the VAN was released by insonation (20 min, 5 MHz, 3 $MPa_{pk-pk}$) and caused ~10× less bacterial colonization.

Further studies measure release from 2 sheaths, which will be encased within small fluid containing plastic pouches; this approach should simplify measurement of released antibiotic, and the results will provide information on the ABX release kinetics. Specifically, a sheath system (6×10 mm with a 1 mm bore) will be inserted into the surgical dead space created during exposure of the spine, the pouch sutured in place, and the area closed. Optimization of US (energy, time) will be based on antibacterial activity as well as spectrophotometric or ELISA determination of ABX concentrations. The goal is to ensure release of ~1-5 mg of ABX.

Figure 8:
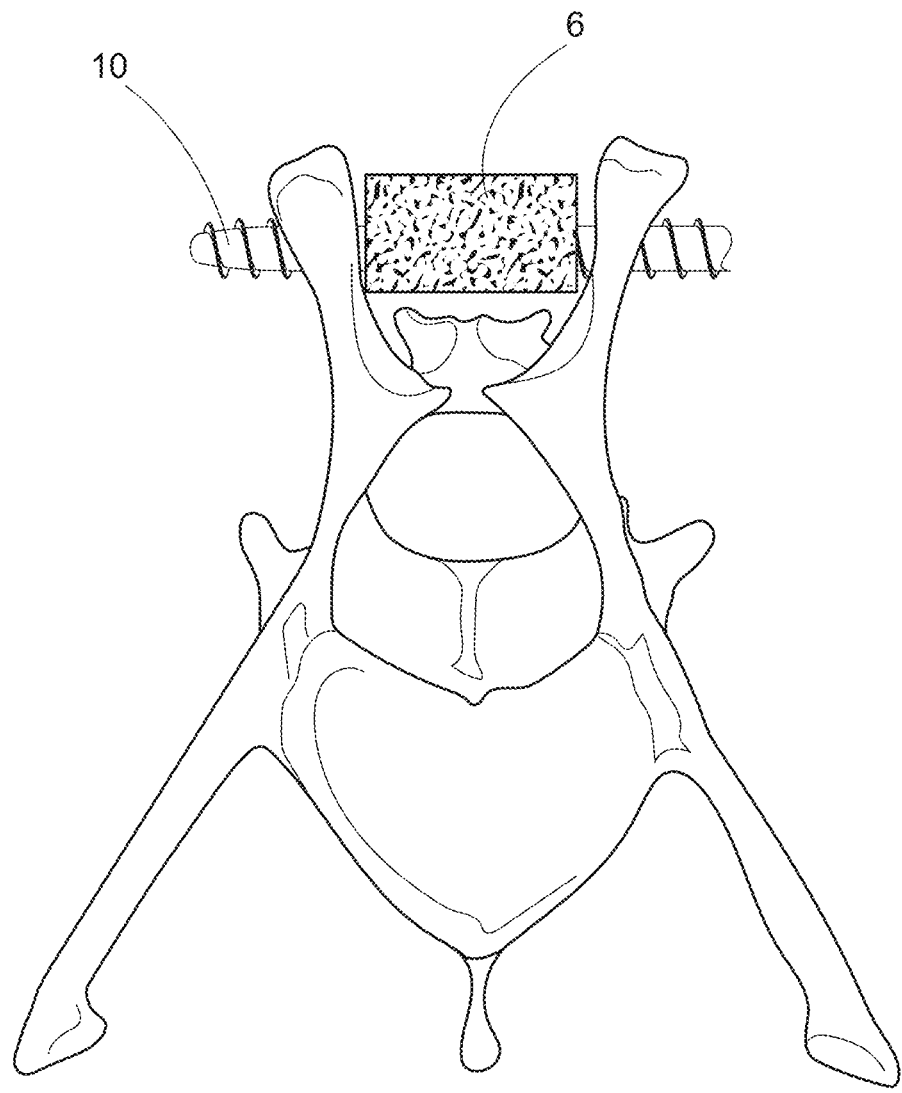
FIG. 8 shows a wire & sheath on rabbit lumbar vertebrae (vertebrae drawing from 66).

In the second set of experiments, the efficacy of these implants in combating infection (S. aureus) is tested in the model of spinal infection[66]. A Kirschner wire will be placed through the target vertebra transverse processes of New Zealand white rabbits, a sheath placed on the wire (FIG. 8) and 100 μl of saline or saline with $5×10^3$ cfu/ml S. aureus, injected onto and around the implant. For each animal, three separate surgical sites will be used with each region having a sheath placed on the wire spanning the transverse processes[66]. The surgical site will be closed with sutures and the animal allowed to recover from surgery for 24 hrs. After 48 hrs., the surgical site will be anesthetized with lidocaine, the rabbit placed under restraint, and US insonation undertaken using the parameters established in the first part of the study. Animals will be sacrificed at days 7 and 28, and clinical signs of infection assessed during dissection. Retrieved hardware and tissues will be tested for infection and for inflammation, cellularity, and bone quality after retrieval.

This study is designed as a 2×3 factorial repeated measures ANOVA with surgical sites nested within rabbits (Table 1), since there are 3 sheath technologies being evaluated (sheath alone as well as sheath loaded with ABX with and without US exposure) under 2 conditions (infected or uninfected). Each of these factors is then assessed at 2 different time points (1 and 4 weeks; the repeated measures).

Experimental Details

Sheath Preparation, Loading, and Sterilization:

For the rabbit experiments, sheaths will be sized down to 6×10 mm cylinders with a 1 mm bore (rabbit spinal sheath). Sheaths will be fabricated, sterilized by autoclaving, and loaded with sterile antibiotic solution. Evaporation of the solution will occur in a covered sterile container in a laminar flow hood. PLA will then be dissolved in $CHCl_3$ and the PEEK sheath coated. The assembled PEEK sheath will be sterilized in the hospital facility with gamma irradiation (while ethylene oxide would leave the contents intact, realistically, gamma irradiation will need to be used to insure that no contamination is present in the interior reservoir). All sheath batches will include two sheaths for assessment of active antibiotic (disc diffusion assay) after sterilization.

Instrumented Fusion:

New Zealand White female rabbits, 2.5-3 kg each, will be used for all procedures. Immediately prior to surgery, the animal will be placed on a warming mat, the back and gluteal region will be shaved, and the surgical area prepped with povidone iodine solution. Draping of the entire surgical area will be used to minimize contamination. Three different identical surgical procedures will be performed on each animal. Each will be performed serially in the same manner at the T13, L3 and L6 vertebrae to allow separation of the sites. Each rabbit surgery will require 60-75 min.

First, the skin over the operative site will be infused using 1 ml of 0.5% bupivacaine prior to making a 2.5 cm skin incision in the midline over each of the desired operative levels. The fascia will be identified and a similar-length fascial incision made in the midline. Next, the spinous process will be identified and removed with the associated paraspinal musculature using a rongeur. The transverse processes will be identified and a Kirschner wire driven from the left through the right transverse process. An antibiotic sheath will be applied for those groups which utilize sheaths. The Kirschner wire will be clipped at the lateral border of the transverse process at the insertion side using a wire cutter. The control or bacterial inocula will be added, fascia will be closed using a running vicryl 2-0 suture and the skin closed using interrupted 2-0 nylon sutures. The other two levels will be prepared in the same manner.

Post-Surgical Care:

Rabbits will be allowed unrestricted ambulation in their cages after recovery from anesthesia and observed daily for activity. All animals will receive analgesia for 3 days after surgery and thereafter as needed. Animals will be monitored for normal mobility, eating, and defecation, signs of infection including wound dehiscence or drainage, elevated temperature, decreasing body weight and evidence of sepsis. Surgical sites will be imaged at the time of sacrifice, with the un-operated levels serving as control.

US Treatment:

At 48 hrs. post-surgery, the surgical site will be anesthetized with lidocaine, and the rabbit placed in a restraint box so that the surgical site is accessible. US will be applied for a time and intensity based on the data in the ex vivo model.

Microbiological and µCT Analysis.

To detect bacteria associated with each Kirschner wire and/or spinal sheath upon its removal, each retrieved implant will be rolled onto a blood agar plate. The plates will be incubated at 37° C. for 24 h, imaged with a digital camera, and further incubated for an additional 48 hrs. to allow growth of any slow-growing organisms, such as resistant bacteria. To further evaluate the adherent bacteria, the wire or sheath will be transferred into 2 ml of Mueller-Hinton Broth, sonicated for 7 min and vortexed for 3 min. Serial dilutions of the bacteria released into MHB will be plated on agar plates, incubated at 37° C., 24-72 hrs., the resultant colonies digitally recorded and the number of colonies counted using ImagePro software. Colony morphology and color will be assessed, as will strain identity (TJU Clinical Micro Lab); antibiotic sensitivity will be determined from said procedures.

Following removal of the Kirschner wire/spinal sheath from each vertebrae, the targeted portion of the spine will be subjected to µCT (Scanco µCT 40, Basel, Switzerland). Scout and cross-sectional views will be collected for each level. Specifically, rabbit spines will be harvested, cut in half so as to fit in sample tubes, fixed in 4% paraformaldehyde, and scanned with µCT on the long axis, with 55 kV energy, 145 µA current and a 200 ms integration time producing a resolution of 16 µm$^3$ voxel size. Each scan will be a minimum of 800 slices encompassing the wire insertion site. 2D sagittal and cross-sectional and 3-dimensional reconstructed views will be examined for characteristics of spinal fusion, and bone quality will be assessed through analysis of relative amounts of high and low density bone[67]. To quantify the effects of bone infection in vivo, three parameters of bone health will be examined by µCT: changes in whole bone volume, changes in high density cortical bone mineralization and changes in low density. Nearly all biological mineralization is detected by µCT in the arbitrary range of 225 to 700 (referred as total bone). This range is split in half, allowing appropriate examination of the upper range (high density bone, 500-700) and the lower range (low density bone, 225-500) independently. The data will be analyzed by two-way ANOVA, taking into account both side and time from operation as covariates.

Histological Analysis: Histological Examination of Immune Response:

Staining: Retrieved spines and surrounding tissues will be clemineralized, paraffin embedded and sectioned. Tissues will be stained with Harris Hemotoxylin and Eosin Y (Fisher Scientific, Kalamazoo, Mich.) to determine cellularity, vascularization and tissue morphology. Sections will also be stained with Wright Geimsa (Fisher Scientific, phosphate buffer pH 6.8) to determine inflammatory cell number and toluidine blue (Sigma, St. Louis, Mo.) to determine mast cell numbers. Sections will also be treated with Antigen Unmasking Solution (1:100) (Vector, Burlingame, Calif.; H-3300) two times (cytospins one time) for 10 minutes in microwaved boiling solution, permeabilized with 0.5% Triton X-100 in PBS for 10 min and blocked with 4% BSA in PBS with 0.1% Tween-20 for 1 hour. Sections will be incubated overnight at 4° C. with primary antibodies recognizing macrophages (CD68), neutrophils (neutrophil el astase), and lymphocytes (CD3, CD4 Antibodies).

Image Acquisition and Analysis:

For each sample, 2-3 sections will be examined. Images of each section (25-30 individual images) will be acquired at a magnification of 20×. Images will be acquired with a Retiga EXi digital-cooled CCD camera with RGB electronic filter (QImaging, Canada) or with an RT Color Spot camera (Diagnostic Instruments, Sterling Heights, Mich.) on either a Nikon Optiphot or on a Nikon E800. Image quantification will be performed with Image Pro Plus software (Mediacybernetics, Silver Spring, Md.), using a customized macro to count DAB stained cells and nuclei of cells stained with hematoxylin. A quantitative value of the inflammatory response will then be presented as the average percent of positive cells (DAB) per total cell number (hematoxylin) normalized to total area. The section results for each block from each anatomical site will be averaged and differences compared. In addition, immunohistochemistry will be performed for IL-6 (R&D Systems), TNF-α (Piercenet) and IL-1β (antibodies-online.com), $T_{reg}$ related cells (CD4+, CD25+; Abdserotec), and IL-1.

Mechanical Testing.

Retrieved spinal sheaths will be mechanically tested in 4-point bending for evidence of mechanical damage or breakdown of the PEEK during implantation. Testing will be performed in accordance with ASTM D790: Standard Test Methods for Flexural Properties of Unreinforced and Reinforced Plastics and Electrical Insulating Materials.

SEM.

The retrieved sheaths will be evaluated in SEM at Drexel for evidence of mechanical damage or breakdown of the PEEK surface during implantation.

Monitoring Blood Chemistry:

At 7 and 28 days, aliquots of blood will be evaluated for antibiotic amounts and the presence of S. aureus (Jefferson Hospital Clinical Laboratory).

CONCLUSIONS

Spinal infections remain a major concern in fusion surgeries. The medical devices described herein, using a reservoir system attached to a spinal fusion rod, wherein the reservoir can be selectively ruptured by US application, provides new mechanisms to treat spinal infection post-surgery through devices that are implanted with the surgical procedure.

However the device can be further utilized in numerous other surgical procedures wherein application of a medicinal compound or composition to a surgical or wound site. The medical compound can include any suitable pharmacologic material including biologic or small molecule compounds, or combinations thereof. The device can utilize one or more different reservoirs attached to or implanted into a wound or surgical site, wherein the one or more reservoirs can be selectively ruptured via the application of a mechanical wave to release the contents of the reservoir to the site.

Therefore, as disclosed herein is a clip having therein a reservoir for holding a therapeutic material, and wherein the reservoir is sealed with a biocompatible polymer material that is capable of being ruptured by an outside force, e.g. US, and wherein upon rupture of the biocompatible polymer material, the contents of the reservoir are released into a surgical site.

Accordingly, methods of treatment for spinal infection are similarly provided, wherein a method includes performing a surgical procedure by inserting a medical device comprising a reservoir system having a pressure responsive membrane that is capable of rupturing under a pressure stimulus. Subsequently, a mechanical wave, such as ultrasound is applied to said surgical site post-surgery, which bursts the pressure responsive membrane to release the contents of the reservoir system to the surgical site. Preferred contents of the reservoir system include biologic and small molecule pharmaceutical products or combinations therefore.

A further method is directed towards a method of providing supratherapeutic levels of a therapeutic material to a wound site comprising: inserting a sheath into a wound site, wherein said sheath is formed from a biocompatible material and comprises a reservoir and a reservoir opening and wherein said sheath is covered by a pressure responsive membrane that is stable in the body for about 7 days but is capable of being ruptured by application of a pressure external to the body; applying an external pressure to the wound site to rupture the membrane and release the contents of the reservoir to the wound site.

BIBLIOGRAPHY

1 Molinari, R. W., Khera, O. A. & Molinari, W. J., 3rd. Prophylactic intraoperative powdered vancomycin and postoperative deep spinal wound infection: 1,512 consecutive surgical cases over a 6-year period. *European Spine Journal* 21 Suppl 4, S476-482, doi:http://dx-.doi.org/10.1007/s00586-011-2104-z (2012).

2 O'Neill, K. R. et al. Reduced surgical site infections in patients undergoing posterior spinal stabilization of traumatic injuries using vancomycin powder. *Spine J* 11, 641-646, doi:10.1016/j.spinee.2011.04.025 (2011).

3 Ghobrial, G. M. et al. Intraoperative vancomycin use in spinal surgery: single institution experience and microbial trends. *Spine (Phila Pa. 1976)* 39, 550-555, doi:10.1097/BRS.0000000000000241 (2014).

4 Hill, B. W., Emohare, O., Song, B., Davis, R. & Kang, M. M. The use of vancomycin powder reduces surgical reoperation in posterior instrumented and noninstrumented spinal surgery. *Acta Neurochir (Wien)* 156, 749-754, doi:10.1007/s00701-014-2022-z (2014).

5 Godi, S. S., Parker, S. L., O'Neill, K. R., Devin, C. J. & McGirt, M. J. Comparative effectiveness and cost-benefit analysis of local application of vancomycin powder in posterior spinal fusion for spine trauma: clinical article. *J. Neurosurg. Spine* 19, 331-335, doi: 10.3171/2013.6.SPINE121105 (2013).

6 Emohare, O. et al. Cost savings analysis of intrawound vancomycin powder in posterior spinal surgery. *Spine J* 14, 2710-2715, doi:10.1016/j.spinee.2014.03.011 (2014).

7 Dastgheyb, S., Parvizi, J., Shapiro, I. M., Hickok, N. J. & Otto, M. Effect of Biofilms on Recalcitrance of Staphylococcal Joint Infection to Antibiotic Treatment. *J Infect Dis*, doi: 10.1093/infdis/jiu1514; First published online: September 1011, 2014, doi:10.1093/infdis/jiu514 (2014).

8 Costerton, J. W., Montanaro, L. & Arciola, C. R. Biofilm in implant infections: its production and regulation. *International Journal of Artificial Organs* 28, 1062-1068 (2005).

9 Antoci, V., Jr. et al. Vancomycin covalently bonded to titanium alloy prevents bacterial colonization. *J Orthop Res* 25, 858-866, doi:10.1002/jor.20348 (2007).

10 Lewis, K. Multidrug tolerance of biofilms and persister cells. *Current Topics in Microbiology & Immunology* 322, 107-131 (2008).

11 Collins, I. et al. The diagnosis and management of infection following instrumented spinal fusion. *Eur Spine J* 17, 445-450, doi:10.1007/s00586-007-0559-8 (2008).

12 Ketonis, C., Parvizi, J., Adams, C. S., Shapiro, I. M. & Hickok, N. J. Topographic features retained after antibiotic modification of Ti alloy surfaces. *Clin. Orthop. Rel. Res.* 467, 1678-1687 (2009).

13 Calderone, R. R., Garland, D. E., Capen, D. A. & Oster, H. Cost of medical care for postoperative spinal infections. *Orthop Clinics North America* 27, 171-182 (1996).

14 Calderone, R. R. & Larsen, J. M., (1): Overview and classification of spinal infections. *Orthop Clinics North America* 27, 1-8 (1996).

15 Calderone, R. R., Thomas, J. C., Haye, W. & Abeles, D. Outcome assessment in spinal infections. *Orthop Clinics North America* 27, 201-205 (1996).

16 Beiner, J. M., Grauer, J., Kwon, B. K. & Vaccaro, A. R. Post-operative wound infections of the spine. *Neurosurgical Focus* 15, 15 (2003).

17 Bible, J. E., Biswas, D. & Devin, C. J. Postoperative infections of the spine. *Am J Orthop* 40, E264-271 (2011).

18 Kurtz, S. M. et al. Infection risk for primary and revision instrumented lumbar spine fusion in the Medicare population. *J Neurosurg Spine* 17, 342-347, doi:10.3171/2012.7.SPINE12203 (2012).

19 Hickok, N. J. & Shapiro, I. M. Immobilized antibiotics to prevent orthopaedic implant infections. *Adv Drug Deliv Rev* 64, 1165-1176, doi:10.1016/j.addr.2012.03.015 (2012).

20 Ketonis, C. et al. Vancomycin bonded to bone grafts prevents bacterial colonization. *Antimicrob Agents Chemother* 55, 487-494, doi:10.1128/AAC.00741-10 (2011).

21 Kurtz, S. M. et al. Retrieval analysis of PEEK rods for posterior fusion and motion preservation. *Eur Spine J* 22, 2752-2759, doi:10.1007/s00586-013-2920-4 (2013).

22 Kurtz, S. M. & Devine, J. N. PEEK biomaterials in trauma, orthopedic, and spinal implants. *Biomaterials* 28, 4845-4869 (2007).

23 Trampuz, A. et al. Sonication of removed hip and knee prostheses for diagnosis of infection. *N Engl J Med* 16, 654-663 (2007).

24 Trampuz, A., Osmon, D. R., Hanssen, A. D., Steckelberg, J. M. & Patel, R. Molecular and antibiofilm approaches to prosthetic joint infection. *Clinical Orthopaedics & Related Research.*, 69-88 (2003).

25 Bjerkan, G., Witso, E. & Bergh, K. Sonication is superior to scraping for retrieval of bacteria in biofilm on titanium and steel surfaces in vitro. *Acta Orthopaedica* 80, 245-250 (2009).

26 He, N. et al. Enhancement of vancomycin activity against biofilms by using ultrasound-targeted microbubble destruction. *Antimicrobial Agents and Chemotherapy* 55, 5331-5337 (2011).

27 Ensing, G. T., Neut, D., van Horn, J. R., van der Mei, H. C. & Busscher, H. J. The combination of ultrasound with antibiotics released from bone cement decreases the viability of planktonic and biofilm bacteria: an in vitro study with clinical strains. *J Antimicrob Chemother* 58, 1287-1290, doi:dk1402 [pii]10.1093/jac/dk1402 (2006).

28 Carmen, J. C. et al. Ultrasonically enhanced vancomycin activity against *Staphylococcus epidermidis* biofilms in vivo. *J Biomater Appl* 18, 237-245, doi:10.1177/0885328204040540 (2004).

29 Otto, M. *Staphylococcus epidermidis*—the 'accidental' pathogen. *Nature Reviews. Microbiology.* 7, 555-567 (2009).

30 Smith, A. W. Biofilms and antibiotic therapy: is there a role for combating bacterial resistance by the use of novel drug delivery systems? *Adv Drug Delivery Rev* 57, 1539-1550 (2005).

31 Chivers, R. A. & Moore, D. R. The effect of molecular weight and crystallinity on the mechanical properties of injection moulded poly(aryl-ether-ether-ketone) resin. *Polymer* 35, 110-116 (1994).

32 Rae, P. J., Brown, E. N. & Orler, E. B. The mechanical properties of poly(ether-ether-ketone) (PEEK) with emphasis on the large compressive strain response. *Polymer* 48, 598-615 (2007).

33 Katzer, A., Marquardt, H., Westendorf, J., Wening, J. V. & von Foerster, G. Polyetheretherketone—cytotoxicity and mutagenicity in vitro. *Biomaterials* 23, 1749-1759 (2002).

34 Gunja, N. J. & Athanasiou, K. A. Biodegradable materials in arthroscopy. *Sports Medicine & Arthroscopy Review* 14, 112-119 (2006).

35 Eisenbrey, J. R. et al. Development and optimization of a doxorubicin loaded poly(lactic acid) contrast agent for ultrasound directed drug delivery. *J Control Release* 143, 38-44, doi:doi: 10.1016/j.jconrel.2009.12.021 (2010).

36 Collis, J. et al. Cavitation microstreaming and stress fields created by microbubbles. *Ultrasonics* 50, 273-279, doi: doi: 10.1016/j.ultras.2009.10.002 (2010).

37 Liu, X. & Wu, J. Acoustic microstreaming around an isolated encapsulated microbubble. *J Acoust Soc Am.* 125, 1319-1330, doi:doi: 10.1121/1.3075552 (2009).

38 Sevit, A. M. et al. Development of an ultrasound-sensitive antimicrobial platform for reducing infection after spinal stabilization surgery. *Proc IEEE IUS* 2014, 1045-1048 (2014).

39 Sevit, A. M. et al. Antibiotic Drug Release PEEK Clip to Combat Surgical Site Infection in Spinal Fusion Surgery. *Second International PEEK Conference*, Accepted Abstract (2014).

40 Yu, X., Zipp, G. & Davidson, G. The effect of temperature and pH on the solubility of quinolone compounds: estimation of heat of fusion. *Pharm. Res.* 11, 522-527 (1994).

41 Biotechnology, S. C. Cefazolin. *CAS* 27164-46-1 (2014).

42 Biotechnology, S. C. Tobramycin Sulfate. *CAS* 76945-27-5 (2014).

43 research, d. O. P. Q. Report to office of generic drugs vancomycin solubility study. *Office Of Testing And Research Center For Drug Evaluation And Research Food And Drug Administration* (2008).

44 Usacheva, M. N., Teichert, M. C. & Biel, M. A. Comparison of the methylene blue and toluidine blue photobactericidal efficacy against gram-positive and gram-negative microorganisms. *Lasers in surgery and medicine* 29, 165-173 (2001).

45 F1877-05e Standard Practice for Characterization of Particles. (ASTM International, 2005).

46 Forsberg, F. et al. Development of an ultrasound-sensitive antimicrobial platform for reducing infection after spinal stabilization surgery. *Proc. IEEE Ultrason Symp.* Accepted (2014).

47 Prasad, Y. V. R. et al. Enhanced intestinal absorption of vancomycin with Labrasol and d-α-tocopheryl PEG 1000 succinate in rats. *International Journal of Pharmaceutics* 250, 181-190, doi:http://dx.doi.org/10.1016/S0378-5173 (02)00544-6 (2003).

48 Bernabeu, E. & Chiappetta, D. A. Vitamin E TPGS Used as Emulsifier in the Preparation of Nanoparticulate Systems. *Journal of Biomaterials and Tissue Engineering* 3, 122-134, doi:10.1166/jbt.2013.1076 (2013).

49 Corveleyn, S. & Remon, J. P. Formulation of a lyophilized dry emulsion tablet for the delivery of poorly soluble drugs. *International Journal of Pharmaceutics* 166, 65-74, doi:http://dx.doi.org/10.1016/S0378-5173 (98)00024-6 (1998).

50 Zimmerli, W. & Sendi, P. Pathogenesis of implant-associated infection: the role of the host. *Semin Immunopathol* 33, 295-306, doi:10.1007/s00281-011-0275-7 (2011).

51 Weinstein, M. A., McCabe, J. P. & Cammisa, F. P., Jr. Postoperative spinal wound infection: a review of 2,391 consecutive index procedures. *J Spinal Disord* 13, 422-426 (2000).

52 Johnson, P. J. & Levin, B. R. Pharmacodynamics, population dynamics, and the evolution of persistence in 53 Keren, I., Mulcahy, L. R. & Lewis, K. Persister eradication: lessons from the world of natural products. *Methods Enzymol* 517, 387-406, doi:10.1016/B978-0-12-404634-4.00019-X (2012).
54 Pitt, W. G. & Ross, S. A. Ultrasound increases the rate of bacterial cell growth. *Biotechnol Prog.* 19, 1038-1044 (2003).
55 Carmen, J. C. et al. Ultrasonic-enhanced gentamicin transport through colony biofilms of *Pseudomonas aeruginosa* and *Escherichia coli*. *J Infect Chemother* 10, 193-199, doi:10.1007/s10156-004-0319-1 (2004).
56 Conner-Kerr, T. et al. The effects of low-frequency ultrasound (35 kHz) on methicillin-resistant *Staphylococcus aureus* (MRSA) in vitro. *Ostomy Wound Management* 56, 32-42 (2010).
57 Malone, C. L. et al. Fluorescent reporters for *Staphylococcus aureus*. *J Microbiol Methods* 77, 251-260, doi: 10.1016/j.mimet.2009.02.011 (2009).
58 Walker, J. N. et al. The *Staphylococcus aureus* ArlRS two-component system is a novel regulator of agglutination and pathogenesis. *PLoS pathogens* 9, e1003819, doi:10.1371/journal.ppat.1003819 (2013).
59 Antoci, V., Jr. et al. Covalently attached vancomycin provides a nanoscale antibacterial surface. *Clin Orthop Relat Res* 461, 81-87, doi: 10.1097/BLO0b013e3181123a50 (2007).
60 Ketonis, C., Barr, S., Adams, C. S., Hickok, N. J. & Parvizi, J. Bacterial colonization of bone allografts: establishment and effects of antibiotics. *Clin Orthop Relat Res* 468, 2113-2121, doi:10.1007/s11999-010-1322-8 (2010).
61 Antoci, V., Jr., Adams, C. S., Hickok, N. J., Shapiro, I. M. & Parvizi, J. Vancomycin bound to Ti rods reduces periprosthetic infection: preliminary study. *Clin Orthop Relat Res* 461, 88-95, doi:10.1097/BLO.0b013e318073c2b2 (2007).
62 Stewart, S. et al. Vancomycin-Modified Implant Surface Inhibits Biofilm Formation and Supports Bone-Healing in an Infected Osteotomy Model in Sheep: A Proof-of-Concept Study. *J Bone Joint Surg Am* 94, 1406-1415, doi:10.2106/JBJS.K.00886 (2012).
63 Antoci, V., Jr., Adams, C. S., Hickok, N. J., Shapiro, I. M. & Parvizi, J. Antibiotics for local delivery systems cause skeletal cell toxicity in vitro. *Clin Orthop Relat Res* 462, 200-206, doi: 10.1097/BLO.0b013 e31811ff866 (2007).
64 Go, J. L., Rothman, S., Prosper, A., Silbergleit, R. & Lerner, A. Spine infections. *Neuroimaging Clinics of North America* 22, 755-772, doi:http://dx.doi.org/10.1016/j.nic.2012.06.002 (2012).
65 Ferry, T. et al. The challenge of infection prevention in spine surgery: an update. *Eur* 23 Suppl 1, S15-19, doi: http://dx.doi.org/10.1007/s00590-013-1232-z (2013).
66 Poelstra, K. A., Barekzi, N. A., Grainger, D. W., Gristina, A. G. & Schuler, T. C. A novel spinal implant infection model in rabbits. *Spine (Phila Pa. 1976)* 25, 406-410 (2000).
67 Freeman, T. A., Patel, P., Parvizi, J., Antoci, V., Jr. & Shapiro, I. M. Micro-CT analysis with multiple thresholds allows detection of bone formation and resorption during ultrasound-treated fracture healing. *J Orthop Res* 27, 673-679, doi:10.1002/jor.20771 (2009).
68. Cutting, K. G. Wound exudate: composition and functions. Br. J. Community Nurs. 8 (9Suppl):4-9 (2003).

What is claimed is:

1. A biocompatible clip comprising a reservoir and a reservoir opening, wherein the reservoir is filled with gas and a therapeutic agent; and wherein the reservoir opening is sealed with a pressure: responsive material that can be ruptured upon application of a force from ultrasonic sound waves to said pressure-responsive material; said clip comprising a concave recess disposed along a longitudinal axis of said clip, wherein said concave recess is suitable for securing said clip to a medical device.

2. The biocompatible clip of claim 1 wherein said clip is made of polyether ether ketone (PEEK).

3. The biocompatible clip of claim 1 wherein said pressure-responsive material is made of polylactic acid (PLA).

4. The biocompatible clip of claim 1, wherein the therapeutic agent is selected from the group consisting of: an antibiotic, anti-viral, pain medication, growth factor, anti-fungal, antimycobacteria chemotherapeutic, osteogenic, non-toxic factor or metabolite, such as ascorbate to increase bone formation, parathyroid hormone, peptides, peptoids, NSAIDs, analgesics, or combinations thereof.

5. The biocompatible clip of claim 1 further comprising a second reservoir component attached thereto and wherein the second reservoir component is sealed with a second pressure-responsive material that has a different rupture profile from the first pressure-responsive material.

6. The biocompatible clip of claim 5 wherein the different rupture profile is formed by using a different pressure-responsive material than is used for the first pressure-responsive material.

7. The biocompatible clip of claim 5 wherein the different rupture profiles for the first and second pressure-responsive material are generated by using a thicker covering of pressure-responsive material for one of the materials.

8. The biocompatible clip of claim 1 wherein the medical device is a spinal fusion rod, and wherein the reservoir is filled with an antibiotic material.

9. A method for treatment of infection at a surgical site comprising:
  a. performing a surgical procedure comprising implanting a device to be inserted into the body, wherein said device comprises at least one biocompatible sheath that is attached to at least a portion of the device and comprises a reservoir filled with gas and a therapeutic material; wherein said sheath is further coated with a pressure-responsive material suitable for being ruptured;
  b. applying ultrasound waves to the site of the surgical procedure, wherein said ultrasound waves causes cavitation of gas bubbles leading to rupturing of the pressure-responsive material, wherein said therapeutic material is thereafter released from said sheath to the surgical site.

10. The method of claim 9 wherein the biocompatible sheath is PEEK.

11. The method of claim 9 wherein the pressure-responsive material is PLA.

12. The method of claim 9, wherein the pressure-responsive material is formed by dipping the sheath into a 50 mg/ml 250 mg/ml PLA/CHCl$_3$ solvent and dipped between 5 and 10 times to form a pressure-responsive coating on the sheath.

13. The method of claim 9, wherein the reservoir contains a therapeutic selected from the group consisting of: an antibiotic, anti-viral, pain medication, growth factor, anti-fungal, antimycobacteria chemotherapeutic, osteogenic, non-toxic factor or metabolite, such as ascorbate to increase bone formation, parathyroid hormone, peptides, peptoids, NSAIDs, analgesics, or combinations thereof.

14. The method of claim 9 further comprising a second biocompatible sheath comprising a reservoir filled with a different therapeutic material and wherein the second biocompatible sheath is coated with a second pressure-responsive material having a different rupture profile than the first pressure-responsive material.

15. An implantable medical device comprising a sheath formed of a polymer material, secured to at least a portion of the implantable medical device, wherein the sheath forms a reservoir attached to or around the implantable medical device, and wherein the reservoir is sealed with a biocompatible pressure-responsive coating; wherein the biocompatible coating is stable for at least 7-day post implantation into a body, and can be mechanically ruptured by application of an exterior pressure generating force, said reservoir filled with gas and a therapeutic material, and wherein said mechanical rupture triggers release of the therapeutic material from the reservoir.

16. The implantable medical device of claim 15 further comprising a second sheath secured to a second portion of the implantable medical device, wherein the second sheath comprises a reservoir sealed with a biocompatible pressure-responsive coating having a different release profile from the first biocompatible pressure-responsive coating.

17. The implantable medical device of claim 15 wherein said polymer material is PEEK and said biocompatible pressure-responsive coating is PLA.

18. The implantable medical device of claim 15 wherein said reservoir is filled with gas and a therapeutic selected from the group consisting of: an antibiotic, anti-viral, pain medication, growth factor, anti-fungal, antimycobacteria chemotherapeutic, osteogenic, non-toxic factor or metabolite, such as ascorbate to increase bone formation, parathyroid hormone, peptides, peptoids, NSAIDs, analgesics, or combinations thereof.

* * * * *